(12) United States Patent
Hubschwerlen et al.

(10) Patent No.: US 8,211,890 B2
(45) Date of Patent: Jul. 3, 2012

(54) 5-AMINO-2-(1-HYDROXY-ETHYL)-TETRAHYDROPYRAN DERIVATIVES

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceuticals, Allschwil (CH)

( * ) Notice: Subject to any disclaimer, the term of this patent is extended or adjusted under 35 U.S.C. 154(b) by 0 days.

(21) Appl. No.: 13/139,179

(22) PCT Filed: Dec. 11, 2009

(86) PCT No.: PCT/IB2009/055689
§ 371 (c)(1),
(2), (4) Date: Jun. 10, 2011

(87) PCT Pub. No.: WO2010/067332
PCT Pub. Date: Jun. 17, 2010

(65) Prior Publication Data
US 2011/0245259 A1      Oct. 6, 2011

(30) Foreign Application Priority Data
Dec. 12, 2008    (WO) .................. PCT/IB2008/055261

(51) Int. Cl.
A61K 31/50       (2006.01)
A61K 31/435      (2006.01)
C07D 237/00      (2006.01)
C07D 241/00      (2006.01)
C07D 513/02      (2006.01)
C07D 471/04      (2006.01)

(52) U.S. Cl. ........ 514/248; 514/301; 514/302; 544/235; 544/354; 546/114; 546/115

(58) Field of Classification Search ................ 514/248, 514/301, 302; 544/235, 354; 546/114, 115
See application file for complete search history.

(56) References Cited

U.S. PATENT DOCUMENTS

| 2010/0137290 A1 | 6/2010 | Gude et al. |
| 2010/0249417 A1 | 9/2010 | Kiyoto et al. |

FOREIGN PATENT DOCUMENTS

| WO | WO 00/21948 | 4/2000 |
| WO | WO 02/056882 | 7/2002 |
| WO | WO 03/087098 | 10/2003 |
| WO | WO 2004/058144 | 7/2004 |
| WO | WO 2004/089947 | 10/2004 |
| WO | WO 2005/019215 | 3/2005 |
| WO | WO 2006/014580 | 2/2006 |
| WO | WO 2006/032466 | 3/2006 |
| WO | WO 2006/046552 | 5/2006 |
| WO | WO 2006/125974 | 11/2006 |
| WO | WO 2007/071936 | 6/2007 |
| WO | WO 2007/081597 | 7/2007 |
| WO | WO 2007/086016 | 8/2007 |
| WO | WO 2007/105154 | 9/2007 |
| WO | WO 2007/115947 | 10/2007 |
| WO | WO 2008/003690 | 1/2008 |
| WO | WO 2008/009700 | 1/2008 |
| WO | WO 2008/126024 | 10/2008 |

OTHER PUBLICATIONS

Hubschwerlen et al., U.S. Appl. No. 11/691,310, filed Mar. 26, 2007.
Gude et al., U.S. Appl. No. 12/595,711, filed Oct. 13, 2009.
Preliminary Amendment in U.S. Appl. No. 11/691,310, filed Mar. 26, 2007.
Preliminary Amendment in U.S. Appl. No. 12/595,711, filed Jan. 12, 2010.
Benz, Comprehensive Organic Synthesis, B.M. Trost, 1. Fleming, Eds; Pergamon Press: New York, vol. 6, pp. 381-417 (1991).
Larock, Comprehensive Organic Transformations, A guide to Functional Group Preparations; 2nd Edition, Wiley-VC; New York, Chichester, Weinheim, Brisbane, Singapore, Toronto, Section: nitriles, carboxylic acids and derivatives, pp. 1941-1949 (1999).
Larock, Comprehensive Organic Transformations, A guide to Functional Group Preparations; 2nd Edition, Wiley-VC; New York, Chichester, Weinheim, Brisbane, Singapore, Toronto, Section: Aldehydes and Ketones (1999).
Larock, Comprehensive Organic Transformations, A guide to Functional Group Preparations; 2nd Edition, Wiley-VC; NeW York, Chichester, Weinheim, Brisbane, Singapore, Toronto, Section: Amines, pp. 1075-1111 (1999).
Gould, International Journal of Pharmaceutics, vol. 33, pp. 201-217 (1986). Index of Remington, The Science and Practice of Pharmacy, 21st Edition, Part 5, "Pharmaceutical Manufacturing" [published by Lippincott Williams & Wilkins]) (2005).
Kriek et al., European Journal of Organic Chemistry, pp. 2418-2427 (2003).

(Continued)

*Primary Examiner* — Rebecca Anderson
*Assistant Examiner* — Samantha Shterengarts
(74) *Attorney, Agent, or Firm* — Hunton & Williams LLP

(57) ABSTRACT

The invention relates to antibacterial compounds of formula I wherein
$R^1$ represents alkoxy (notably methoxy);
$R^2$ represents H or F;
each of $R^3$, $R^4$, $R^5$ and $R^6$ represents independently H or D;
V represents CH and W represents CH or N, or V represents N and W represents CH;
Y represents CH or N;
Z represents O, S or $CH_2$; and
A represents $CH_2$, $CH_2CH_2$ or $CD_2CD_2$;
and salts of such compounds.

17 Claims, No Drawings

OTHER PUBLICATIONS

Sato et al., Tetrahedron, vol. 60, pp. 7899-7906 (2004).
Kolb et al., Chemical Reviews, vol. 94, No. 8, pp. 2483-2547 (1994).
Mancuso et al., The Journal of Organic Chemistry, vol. 43, No. 12, pp. 2480-2482 (1978).
Dess et al., The Journal of Organic Chemistry, vol. 48, No. 22, pp. 4155-4156 (1983).
Greene et al., Protecting Groups in Organic Synthesis, 3$^{rd}$ Edition, pp. 464-653 (1999).
Wikler et al., Clinical and Laboratory Standards Institute, Document M7-A7, vol. 26, No. 2, Wayne, PA, USA (2006).
Ley et al., Synthesis, vol. 7, pp. 639-666 (1994).
Blakemore, Journal of the Chemical Society, pp. 2563-2585 (2002).
Talbot et al., Clinical Infectious Diseases, vol. 42, pp. 657-668 (2006).
International Search Report for International Application No. PCT/IB2009/055689, mailed Apr. 1, 2010.
Written Opinion for International Application No. PCT/IB2009/055689, mailed Apr. 1, 2010.

5-AMINO-2-(1-HYDROXY-ETHYL)-TETRAHYDROPYRAN DERIVATIVES

CROSS-REFERENCE TO RELATED APPLICATIONS

This application is the national phase application of PCT/IB2009/055689, filed Dec. 11, 2009, which claims the benefit of PCT/IB2008/055261, filed Dec. 12, 2008, the contents of each are hereby incorporated by reference in their entirety.

FIELD OF THE INVENTION

The present invention concerns novel 5-amino-2-(1-hydroxy-ethyl)-tetrahydropyran derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

BACKGROUND OF THE INVENTION

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

BRIEF SUMMARY OF THE INVENTION

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:
- *S. aureus* is resistant to B-lactams, quinolones and now even to vancomycin;
- *S. pneumoniae* is becoming resistant to penicillin or quinolone antibiotics and even to new macrolides;
- Enteroccocci are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome multidrug-resistant Gram-negative bacilli such as *A. baumannii*, ESBL-producing *E. coli* and *Klebsiella* species and *Pseudomonas aeruginosa* (*Clinical Infectious Diseases* (2006), 42, 657-68).

In addition, microorganisms that are causing persistent infections are increasingly being recognized as causative agents or cofactors of severe chronic diseases like peptic ulcers or heart diseases.

WO 2006/032466 discloses antibacterial compounds of formula (A1)

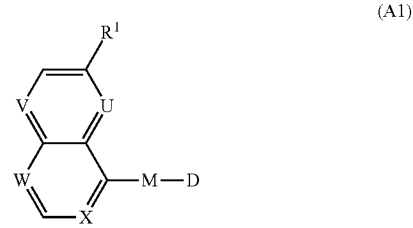

(A1)

wherein $R^1$ represents notably alkoxy, halogen or cyano;
one or two of U, V, W and X represent(s) N, the remaining represent CH, or, in the case of U, V and/or W, may also represent $CR^a$ and, in the case of X, may also represent $CR^b$;
$R^a$ represents halogen;
$R^b$ represents halogen or alkoxy;
D can notably represent a group of the formula

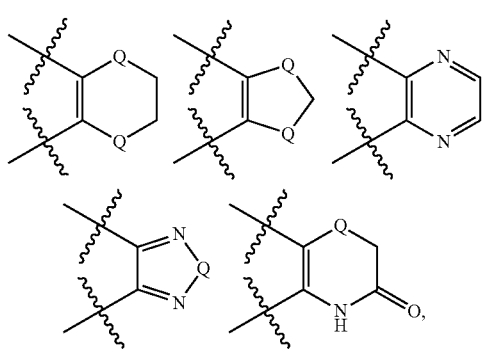

wherein P is a ring selected from

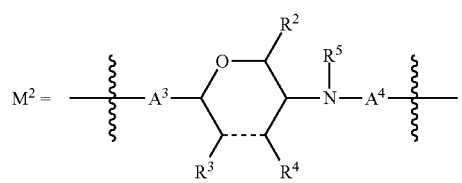

Q is O or S;
K, Y and Z are each independently N or $CR^3$; and
$R^3$ is hydrogen or halogen (and in particular hydrogen or fluorine);
M is notably the group $M^2$:

$$M^2 = \text{—} A^3 \text{—} \underset{R^3 \ R^4}{\underset{|}{\text{ring}}} \text{—} N(R^5) \text{—} A^4 \text{—}$$

wherein
$A^3$ represents NHCO, $CH_2CH_2$, CH=CH, $COCH_2$, $CH(OH)CH_2$, $CH_2CH(OH)$, $CH(OH)CH(OH)$ or $OCH_2$;
$A^4$ represents $CH_2$, CO, $CH_2CH$=CH, COCH=CH or $CH_2CONH$;
$R^2$ can notably represent hydrogen;

R³ and R⁴ can notably each represent hydrogen;
R⁵ can notably represent hydrogen; and
the dotted line represents a single bond or, when R³ and R⁴ represent hydrogen, also a double bond.

Among the compounds specifically disclosed in WO 2006/032466, there is (at Example 187) the compound of the formula (E187):

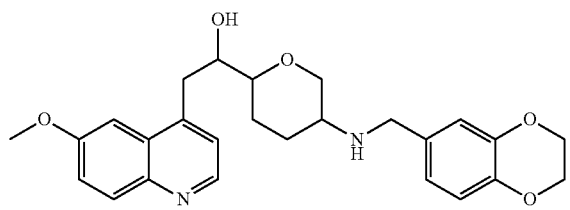

(E187)

Besides, WO 2006/125974 also discloses generically compounds of formula (A1) as described above, including (at Example 1) the compound of formula (E1):

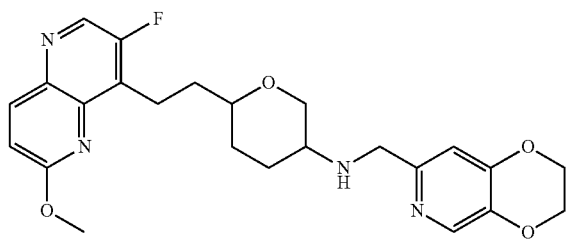

(E1)

WO 2007/080016 discloses compounds that have a formula very similar to that of formula (A1) above with respect to all side chains, with the exception of the side chain R².

WO 2007/105154 discloses specific compounds of formula (A1) above, including (at Example 21) the compound of the formula (E21):

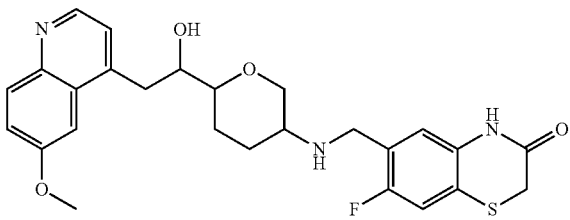

(E21)

Although the compounds of formula (E187), (E21) or (E1) may have interesting antibacterial properties, they are not suitable for use in man because they are very likely to induce prolongation of the QT interval and thus ventricular dysrhythmia, a serious adverse event that may cause death of the patient.

The Applicants have now found particular 5-amino-2-(1-hydroxy-ethyl)-tetrahydropyran antibiotic derivatives corresponding to the formula I described hereafter. Unlike the previously known compounds of related structure, the compounds of formula I have a low hERG K⁺ channel inhibition, which makes them less likely to prolong the QT interval and to bring about ventricular dysrhythmia.

DETAILED DESCRIPTION OF PREFERRED EMBODIMENTS

Various embodiments of the invention are presented hereafter:

i) The invention firstly relates to compounds of formula I

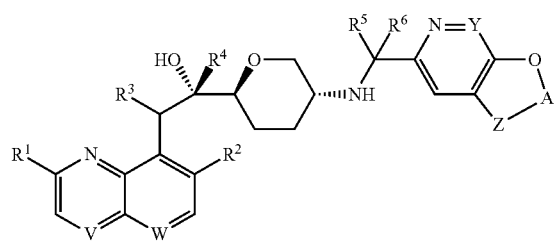

I wherein
R¹ represents alkoxy (notably methoxy);
R² represents H or F;
each of R³, R⁴, R⁵ and R⁶ represents independently H or D;
V represents CH and W represents CH or N or V represents N and W represents CH;
Y represents CH or N;
Z represents O, S or CH₂; and
A represents CH₂, CH₂CH₂ or CD₂CD₂;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. Representative examples of alkyl groups include methyl, ethyl, propyl, iso-propyl, n-butyl, iso-butyl, sec-butyl and tent-butyl. The term "($C_x$-$C_y$)alkyl" (x and y each being an integer) refers to an alkyl group as defined before containing x to y carbon atoms.

The term "alkoxy", used alone or in combination, refers to a straight or branched chain alkoxy group containing from one to four carbon atoms. The term "($C_x$-$C_y$)alkoxy" (x and y each being an integer) refers to an alkoxy group as defined before containing x to y carbon atoms. For example, a ($C_1$-$C_3$)alkoxy group contains from one to three carbon atoms. Representative examples of alkoxy groups include methoxy, ethoxy, n-propoxy and iso-propoxy. Preferred are methoxy and ethoxy.

The term "halogen" refers to fluorine, chlorine, bromine or iodine, preferably to fluorine or chlorine.

The symbol "D" refers to a deuterium atom, i.e. the ²H isotope of hydrogen.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of from 20 to 30° C., and preferably 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

ii) The invention furthermore relates to compounds of formula I as defined in embodiment i) that are also compounds of formula $I_P$

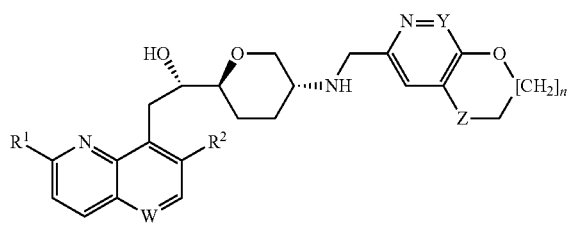

$I_P$ wherein
$R^1$ represents alkoxy (notably methoxy);
$R^2$ represents H or F;
W represents CH or N;
Y represents CH or N;
Z represents O, S or $CH_2$; and
n represents 0 or 1;
and to salts (in particular pharmaceutically acceptable salts) of compounds of formula $I_P$.

iii) In particular, the invention relates to compounds of formula $I_{CE}$, i.e. to compounds of formula I according to embodiment i) wherein:
$R^1$ represents $(C_1-C_3)$alkoxy (particularly methoxy); and
at most one of $R^3$, $R^4$, $R^5$ and $R^6$ represents D and A represents $CH_2$ or $CH_2CH_2$, or each of $R^3$, $R^4$, $R^5$ and $R^6$ represents H and A represents $CH_2$, $CH_2CH_2$ or $CD_2CD_2$;
as well as to salts (in particular pharmaceutically acceptable salts) of such compounds of formula $I_{CE}$.

iv) The invention furthermore relates to compounds of formula $I_{CEP}$, i.e. to compounds of formula $I_P$ according to embodiment ii) wherein $R^1$ represents $(C_1-C_3)$alkoxy (particularly methoxy) and n may represent 0 only if Z represents S, as well as to salts (in particular pharmaceutically acceptable salts) of such compounds of formula $I_{CEP}$.

v) According to a preferred embodiment of this invention, the compounds of formula I as defined in one of embodiments i) to iv) above will be such that $R^1$ is methoxy or ethoxy (particularly methoxy).

vi) According to one variant of this invention, the compounds of formula I as defined in one of embodiments i) to v) above will be such that $R^2$ represents H.

vii) According to another variant of this invention, the compounds of formula I as defined in one of embodiments i) to v) above will be such that $R^2$ represents F.

viii) According to one main embodiment of this invention, the compounds of formula I as defined in one of embodiments i) to vii) above will be such that W represents N.

ix) According to another main embodiment of this invention, the compounds of formula I as defined in one of embodiments i) to vii) above will be such that W represents CH.

x) According to one sub-embodiment of this invention, the compounds of formula I as defined in one of embodiments i) to ix) above will be such that Y represents CH.

xi) According to another sub-embodiment of this invention, the compounds of formula I as defined in one of embodiments i) to ix) above will be such that Y represents N.

xii) One main variant of this invention relates to compounds of formula I as defined in one of embodiments i) to xi) wherein Z represents O.

xiii) According to one sub-variant of main variant xii), the compounds of formula I as defined in main variant xii) above will be such that:
  these compounds are compounds of formula I as defined in embodiment i) or iii) or as defined in embodiment i) or iii) taken together with any of embodiments v) to xi) and A represents $CH_2$; or
  these compounds are compounds of formula I as defined in embodiment ii) or iv) or as defined in embodiment ii) or iv) taken together with any of embodiments v) to xi) and n represents 0.

xiv) According to another sub-variant of main variant xii), the compounds of formula I as defined in main variant xii) above will be such that:
  these compounds are compounds of formula I as defined in embodiment i) or iii) or as defined in embodiment i) or iii) taken together with any of embodiments v) to xi) and A represents $CH_2CH_2$; or
  these compounds are compounds of formula I as defined in embodiment ii) or iv) or as defined in embodiment ii) or iv) taken together with any of embodiments v) to xi) and n represents 1.

xv) According to yet another sub-variant of main variant xii), the compounds of formula I as defined in main variant xii) above will be compounds of formula I as defined in embodiment i) or iii) or as defined in embodiment i) or iii) taken together with any of embodiments v) to xi) and A will represent $CD_2CD_2$.

xvi) Another main variant of this invention relates to compounds of formula I as defined in one of embodiments i) to xi) wherein Z represents S.

xvii) According to one sub-variant of main variant xvi), the compounds of formula I as defined in main variant xvi) above will be such that:
  these compounds are compounds of formula I as defined in embodiment i) or iii) or as defined in embodiment i) or iii) taken together with any of embodiments v) to xi) and A represents $CH_2$; or
  these compounds are compounds of formula I as defined in embodiment ii) or iv) or as defined in embodiment ii) or iv) taken together with any of embodiments v) to xi) and n represents 0.

xviii) According to another sub-variant of main variant xvi), the compounds of formula I as defined in main variant xvi) above will be such that:
  these compounds are compounds of formula I as defined in embodiment i) or iii) or as defined in embodiment i) or iii) taken together with any of embodiments v) to xi) and A represents $CH_2CH_2$; or
  these compounds are compounds of formula I as defined in embodiment ii) or iv) or as defined in embodiment ii) or iv) taken together with any of embodiments v) to xi) and n represents 1.

xix) According to yet another sub-variant of main variant xvi), the compounds of formula I as defined in main variant xvi) above will be compounds of formula I as defined in embodiment i) or iii) or as defined in embodiment i) or iii) taken together with any of embodiments v) to xi) and A will represent $CD_2CD_2$.

xx) Yet another main variant of this invention relates to compounds of formula I as defined in one of embodiments i) to xi) wherein Z represents $CH_2$.

xxi) According to one sub-variant of main variant xx), the compounds of formula I as defined in main variant xx) above will be such that:
- these compounds are compounds of formula I as defined in embodiment i) or iii) or as defined in embodiment i) or iii) taken together with any of embodiments v) to xi) and A represents $CH_2$; or
- these compounds are compounds of formula I as defined in embodiment ii) or iv) or as defined in embodiment ii) or iv) taken together with any of embodiments v) to xi) and n represents 0.

xxii) According to another sub-variant of main variant xx), the compounds of formula I as defined in main variant xx) above will be such that:
- these compounds are compounds of formula I as defined in embodiment i) or iii) or as defined in embodiment i) or iii) taken together with any of embodiments v) to xi) and A represents $CH_2CH_2$; or
- these compounds are compounds of formula I as defined in embodiment ii) or iv) or as defined in embodiment ii) or iv) taken together with any of embodiments v) to xi) and n represents 1.

xxiii) According to yet another sub-variant of main variant xx), the compounds of formula I as defined in main variant xx) above will be compounds of formula I as defined in embodiment i) or iii) or as defined in embodiment i) or iii) taken together with any of embodiments v) to xi) and A will represent $CD_2CD_2$.

xxiv) Another embodiment of this invention relates to compounds of formula I as defined in embodiment i) or iii) or as defined in embodiment i) or iii) taken together with any of embodiments v) to xxiii) wherein V represents CH and W represents CH or N.

xxv) Another embodiment of this invention furthermore relates to compounds of formula I as defined in embodiment i) or iii) or as defined in embodiment i) or iii) taken together with any of embodiments v) to xxiii) wherein V represents N and W represents CH.

xxvi) Another embodiment of this invention relates to compounds of formula I as defined in one of embodiments i), iii), v) to xiv), xvi) to xviii), xx) to xxii), xxiv) and xxv) wherein each of $R^3$, $R^4$, $R^5$ and $R^6$ represents H and A represents $CH_2$ or $CH_2CH_2$, all these compounds being hereafter referred to as compounds of formula $I_H$.

xxvii) According to a particular sub-embodiment of embodiment xxvi), the compounds of formula I as defined in embodiment xxvi) will be such that V represents CH and W represents CH or N.

xxviii) In particular, the compounds of formula I as defined in embodiment xxvii) will be such that:
V represents CH and W represents N;
$R^1$ represents methoxy;
Z represents O or S (preferably O); and
A represents $CH_2CH_2$.

xxix) According to another particular sub-embodiment of embodiment xxvi), the compounds of formula I as defined in embodiment xxvi) will be such that V represents N and W represents CH.

xxx) In particular, the compounds of formula I as defined in embodiment xxix) will be such that:
$R^1$ represents methoxy;
Y represents N;
Z represents O or S (preferably S); and
A represents $CH_2CH_2$.

xxxi) Another embodiment of this invention relates to compounds of formula I as defined in one of embodiments i), iii), v) to xiv), xvi) to xviii), xx) to xxii), xxiv) and xxv) wherein:
either one of $R^3$, $R^4$, $R^5$ and $R^6$ represents D, the others of $R^3$, $R^4$, $R^5$ and $R^6$ each represent H and A represents $CH_2$ or $CH_2CH_2$,
or each of $R^3$, $R^4$, $R^5$ and $R^6$ represents H and A represents $CD_2CD_2$, all these compounds being hereafter referred to as compounds of formula $I_D$.

xxxii) According to a particular sub-embodiment of embodiment xxxi), the compounds of formula I as defined in embodiment xxxi) will be such that V represents CH and W represents CH or N.

xxxiii) In particular, the compounds of formula I as defined in embodiment xxxii) will be such that:
V represents CH and W represents N;
$R^1$ represents methoxy;
Z represents O or S (preferably O); and
A represents $CH_2CH_2$ or $CD_2CD_2$.

xxxiv) According to a particular sub-embodiment of embodiment xxxi), the compounds of formula I as defined in embodiment xxxi) will be such that V represents N and W represents CH.

xxxv) In particular, the compounds of formula I as defined in embodiment xxxiv) will be such that:
$R^1$ represents methoxy;
Y represents N;
Z represents O or S (preferably S); and
A represents $CH_2CH_2$ or $CD_2CD_2$.

xxxvi) Particularly preferred are the following compounds of formula I as defined in one of embodiments i) to iv):
- (1S)-1-{(2S,5R)-5-[(2,3-dihydro-[1,4]dioxino[2,3-c]pyridin-7-ylmethyl)-amino]-tetrahydro-pyran-2-yl}-2-(6-methoxy-[1,5]naphthyridin-4-yl)-ethanol;
- (1S)-1-{(2S,5R)-5-[(6,7-dihydro-[1,4]dioxino[2,3-c]pyridazin-3-ylmethyl)-amino]-tetrahydro-pyran-2-yl}-2-(6-methoxy-[1,5]naphthyridin-4-yl)-ethanol;
- (1S)-1-{(2S,5R)-5-[(2,3-dihydro-[1,4]dioxino[2,3-c]pyridin-7-ylmethyl)-amino]-tetrahydro-pyran-2-yl}-2-(3-fluoro-6-methoxy-[1,5]naphthyridin-4-yl)-ethanol;
- (1S)-1-{(2S,5R)-5-[(6,7-dihydro-[1,4]dioxino[2,3-c]pyridazin-3-ylmethyl)-amino]-tetrahydro-pyran-2-yl}-2-(3-fluoro-6-methoxy-[1,5]naphthyridin-4-yl)-ethanol;
- (1S)-1-{(2S,5R)-5-[(2,3-dihydro-[1,4]dioxino[2,3-c]pyridin-7-ylmethyl)-amino]-tetrahydro-pyran-2-yl}-2-(7-fluoro-2-methoxy-quinolin-8-yl)-ethanol;
- (1S)-1-{(2S,5R)-5-[(2,3-dihydro-4-oxa-1-thia-6-aza-naphthalen-7-ylmethyl)-amino]-tetrahydro-pyran-2-yl}-2-(3-fluoro-6-methoxy-[1,5]naphthyridin-4-yl)-ethanol;
- (1S)-1-{(2S,5R)-5-[(2,3-dihydro-4-oxa-1-thia-6-aza-naphthalen-7-ylmethyl)-amino]-tetrahydro-pyran-2-yl}-2-(7-fluoro-2-methoxy-quinolin-8-yl)-ethanol;
- (1S)-2-(3-fluoro-6-methoxy-[1,5]naphthyridin-4-yl)-1-{(2S,5R)-5-[(3-oxa-1-thia-5-aza-indan-6-ylmethyl)-amino]-tetrahydro-pyran-2-yl}-ethanol;
- (1S)-2-(7-fluoro-2-methoxy-quinolin-8-yl)-1-{(2S,5R)-5-[(3-oxa-1-thia-5-aza-indan-6-ylmethyl)-amino]-tetrahydro-pyran-2-yl}-ethanol;

(1S)-1-{(2S,5R)-5-[(3,4-dihydro-2H-pyrano[2,3-c]pyridin-6-ylmethyl)-amino]-tetrahydro-pyran-2-yl}-2-(3-fluoro-6-methoxy-[1,5]naphthyridin-4-yl)-ethanol;

as well as the salts (in particular the pharmaceutically acceptable salts) thereof.

xxxvii) Further particularly preferred compounds of formula I as defined in embodiment i) or iii) are the following:

(1S)-1-{(2S,5R)-5-[(6,7-dihydro-8-oxa-5-thia-1,2-diazanaphthalen-3-ylmethyl)-amino]-tetrahydro-pyran-2-yl}-2-(3-fluoro-6-methoxy-[1,5]naphthyridin-4-yl)-ethanol;

(1S)-1-{(2S,5R)-5-[(2,3-dihydro-[1,4]dioxino[2,3-c]pyridin-7-ylmethyl)-amino]-tetrahydro-pyran-2-yl}-2-(6-fluoro-3-methoxy-quinoxalin-5-yl)-ethanol;

(1S)-1-{(2S,5R)-5-[(6,7-dihydro-[1,4]dioxino[2,3-c]pyridazin-3-ylmethyl)-amino]-tetrahydro-pyran-2-yl}-2-(6-fluoro-3-methoxy-quinoxalin-5-yl)-ethanol;

(1S)-1-{(2S,5R)-5-[(2,3-dihydro-4-oxa1-thia-6-azanaphthalen-7-ylmethyl)-amino]-tetrahydro-pyran-2-yl}-2-(6-fluoro-3-methoxy-quinoxalin-5-yl)-ethanol;

(1S)-1-{(2S,5R)-5-[(6,7-dihydro-8-oxa-5-thia-1,2-diazanaphthalen-3-ylmethyl)-amino]-tetrahydro-pyran-2-yl}-2-(6-fluoro-3-methoxy-quinoxalin-5-yl)-ethanol;

(1S)-1-((2S,5R)-5-(((2,3-dihydro-[1,4]dioxino[2,3-c]pyridin-7-yl)methyl-d1)amino)tetrahydro-2H-pyran-2-yl)-2-(3-fluoro-6-methoxy-1,5-naphthyridin-4-yl)ethanol;

(1S)-1-((2S,5R)-5-(((2,3-dihydro-[1,4]dioxino-2,2,3,3-d4-[2,3-c]pyridin-7-yl)methyl)amino)tetrahydro-2H-pyran-2-yl)-2-(3-fluoro-6-methoxy-1,5-naphthyridin-4-yl)ethanol;

(1S)-1-((2S,5R)-5-(((2,3-dihydro-[1,4]dioxino[2,3-c]pyridin-7-yl)methyl)amino)tetrahydro-2H-pyran-2-yl)-2-(3-fluoro-6-methoxy-1,5-naphthyridin-4-yl)ethanol-1-d1;

(S)-1-((2S,5R)-5-(((2,3-dihydro-[1,4]oxathiino[2,3-c]pyridin-7-yl)methyl-d1)amino)tetrahydro-2H-pyran-2-yl)-2-(3-fluoro-6-methoxy-1,5-naphthyridin-4-yl)ethanol;

(1S)-1-((2S,5R)-5-(((2,3-dihydro-[1,4]dioxino-[2,3-c]pyridin-7-yl)methyl)amino)tetrahydro-2H-pyran-2-yl)-2-(3-fluoro-6-methoxy-1,5-naphthyridin-4-yl)ethanol-2-d1;

(S)-1-((2S,5R)-5-(((2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-2-d1;

(S)-1-((2S,5R)-5-(((2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-1-d1;

(S)-1-{(2S,5R)-5-[(6,7-dihydro-8-oxa-5-thia-1,2-diazanaphthalen-3-ylmethyl-d1)-amino]-tetrahydro-pyran-2-yl}-2-(3-fluoro-6-methoxy-[1,5]naphthyridin-4-yl)-ethanol;

(15)-1-((2S,5R)-5-(((2,3-dihydro-[1,4]dioxino[2,3-c]pyridin-7-yl)methyl-d2)amino)tetrahydro-2H-pyran-2-yl)-2-(3-fluoro-6-methoxy-1,5-naphthyridin-4-yl)ethanol;

as well as the salts (in particular the pharmaceutically acceptable salts) thereof xxxviii) The invention further relates to the compounds of formula I as defined in embodiment i) or iii) which are selected from the group consisting of the compounds listed in embodiment xxxvi) and the compounds listed in embodiment xxxvii). In particular, it also relates to the groups of compounds of formula I selected from the group consisting of the compounds listed in embodiment xxxvi) and the compounds listed in embodiment xxxvii), which groups of compounds furthermore correspond to one of embodiments v) to xxxv), as well as to the salts (in particular the pharmaceutically acceptable salts) of such compounds. The invention moreover relates to any individual compound of formula I selected from the group consisting of the compounds listed in embodiment xxxvi) and the compounds listed in embodiment xxxvii), and to the salts (in particular the pharmaceutically acceptable salts) of such individual compound.

The compounds of formula I according to the invention, i.e. according to one of embodiments i) to xxxviii), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*;

intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament for the treatment of infections that are mediated by bacteria such as *E. coli*, *Klebsiella pneumoniae* and other *Enterobacteriaceae*, *Acinetobacter* spp. including *Acinetobacter baumanii*, *Stenothrophomonas maltophilia*, *Neisseria meningitidis*, *Bacillus cereus*, *Bacillus anthracis*, *Clostridium difficile*, *Corynebacterium* spp., *Propionibacterium acnes* and bacteroide spp.

The compounds of formula I according to the present invention are further useful to treat protozoal infections caused by *Plasmodium malaria*, *Plasmodium falciparum*, *Toxoplasma gondii*, *Pneumocystis carinii*, *Trypanosoma brucei* and *Leishmania* spp.

The present list of pathogens is to be interpreted merely as examples and in no way as limiting.

The compounds of fomula I according to this invention, or the pharmaceutically acceptable salts thereof, may be used for the preparation of a medicament, and are suitable, for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I in this text (and notably in the embodiments presented above) is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient comprising the administration to said patient of a pharmaceutically active amount of a compound of formula I or a pharmaceutically acceptable salt thereof.

Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_P$, $I_{CE}$, $I_{CEP}$, $I_H$ and $I_D$.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations:

The following abbreviations are used throughout the specification and the examples:

| | |
|---|---|
| Ac | acetyl |
| AcOH | acetic acid |
| AD-mix α | 1,4-bis(dihydroquinine)phthalazine, $K_3Fe(CN)_6$, $K_2CO_3$ and $K_2OsO_4 \cdot 2H_2O$ |
| AD-mix β | 1,4-bis(dihydroquinidine)phthalazine, $K_3Fe(CN)_6$, $K_2CO_3$ and $K_2OsO_4 \cdot 2H_2O$ |
| Alloc | allyloxycarbonyl |
| aq. | aqueous |
| Boc | tert-butoxycarbonyl |
| Cbz | benzyloxycarbonyl |
| CC | column chromatography over silica gel |
| DCE | 1,2-dichloroethane |
| DCM | dichloromethane |
| DIPEA | N,N-diisopropylethylamine |
| DMAP | 4-dimethylaminopyridine |
| DME | 1,2-dimethoxyethane |
| DMF | N,N-dimethylformamide |
| DMSO | dimethylsulfoxide |
| EA | ethyl acetate |
| EDC | 1-ethyl-3-(3-dimethylaminopropyl) carbodiimide hydrochloride |
| ESI | Electron Spray Ionisation |
| eq. | equivalent |
| ether | diethyl ether |
| Et | ethyl |
| EtOH | ethanol |
| Fmoc | 9-fluorenylmethoxycarbonyl |
| HATU | O-(7-azabenzotriazol-1-yl)-N,N,N',N'-tetramethyluronium hexafluorophosphate |
| Hex | hexane |
| Hept | heptane |
| HOBT | 1-hydroxybenzotriazole |
| KHMDS | potassium hexamethyldisilazide |
| LC | liquid chromatography |
| LiHMDS | lithium hexamethyldisilazide |
| Me | methyl |
| MeCN | acetonitrile |
| MeOH | methanol |
| MS | Mass Spectroscopy |
| Ms | methanesulfonyl (mesyl) |
| n-BuLi | n-butyl lithium |
| org. | organic |
| Pd/C | palladium on carbon |
| $Pd/CaCO_3$ | palladium on calcium carbonate |
| $Pd(OH)_2/C$ | palladium dihydroxide on carbon |
| Ph | phenyl |
| Pyr | pyridine |
| rac | racemic |
| rt | room temperature |
| sat. | saturated |
| TBAF | tetrabutylammonium fluoride |
| TBDMS | tert-butyldimethylsilyl |
| TBDPS | tert-butyldiphenylsilyl |
| TBME | tert-butylmethylether |
| tBu | tert-butyl |
| T3P | propylphosphonic anhydride |
| TEA | triethylamine |
| Tf | trifluoromethanesulfonyl (triflyl) |
| TFA | trifluoroacetic acid |
| THF | tetrahydrofuran |
| Ts | para-toluenesulfonyl |

General Reaction Techniques:

General Reaction Technique 1 (Reduction of a Ketone or an Aldehyde into an Alcohol):

The ketone or the aldehyde is reduced with a boron or aluminium hydride reducing agent such as LiBH$_4$, NaBH$_4$ or LiAlH$_4$ in a solvent such as THF between −20° C. and 40° C. If deuterated alcohol derivatives are desired, NaBD$_4$ or LiAlH$_4$ shall be used as reducing agent. Further general methods to reduce carbonyl groups as well as asymmetric reduction methods have been described in *Comprehensive Organic Transformations. A guide to Functional Group Preparations*, 2nd Edition, R. C. Larock, Wiley-VC, New York, Chichester, Weinheim, Brisbane, Singapore, Toronto (1999), Section alcohols and phenols, p. 1075-1087 and p. 1097-1110.

General Reaction Technique 2 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBHCN$_3$, or NaBH(OAc)$_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

General Reaction Technique 3 (Amine Deprotection):

The benzyl carbamates are deprotected by hydrogenolysis over a noble metal catalyst (e.g. Pd/C). The Boc group is removed under acidic conditions such as HCl in an org. solvent such as EA, or TFA neat or diluted in a solvent such DCM. The Alloc group is removed in presence of tetrakis (triphenylphosphine)palladium(0) in presence of an allyl cation scavenger such as morpholine, dimedone or tributyltin hydride between 0° C. and 50° C. in a solvent such as THF. The N-benzyl protected amines are deprotected by hydrogenolysis over a noble metal catalyst (e.g. Pd(OH)$_2$ on charcoal). Further general methods to remove amine protecting groups have been described in *Protecting Groups in Organic Synthesis*, 3$^{rd}$ Ed (1999), 494-653; T. W. Greene, P.G.M. Wuts (Publisher: John Wiley and Sons, Inc., New York).

General Reaction Technique 4 (Amide Formation):

The carboxylic acid is reacted with the amine or alkoxyalkylamine in presence of an activating agent such as DCC, EDC, HOBT, T3P, HATU or di-(N-succinimidyl)-carbonate, in a dry aprotic solvent such as DCM, MeCN or DMF between −20° C. and +60° C. (see G. Benz in Comprehensive Organic Synthesis, B. M. Trost, I. Fleming, Eds; Pergamon Press: New York (1991), vol. 6, p. 381). Alternatively, the carboxylic acid can be activated by conversion into its corresponding acid chloride by reaction with oxalyl chloride or thionyl chloride neat or in a solvent like DCM between 20° and +60° C. Further activating agents can be found in *Comprehensive Organic Transformations. A guide to Functional Group Preparations,* 2nd Edition, R. C. Larock, Wiley-VC; New York, Chichester, Weinheim, Brisbane, Singapore, Toronto (1999), Section nitriles, carboxylic acids and derivatives, p. 1941-1949.

General Reaction Technique 5 (Amine Protection):

Amines are usually protected as carbamates such as Alloc, Cbz or Boc. They are obtained by reacting the amine with allyl or benzyl chloroformate or di tent-butyl dicarbonate in presence of a base such as NaOH, TEA, DMAP or imidazole. They can also be protected as N-benzyl derivatives by reaction with benzyl bromide or chloride in presence of a base such as Na$_2$CO$_3$ or TEA. Alternatively, N-benzyl derivatives can be obtained through reductive amination in presence of benzaldehyde (see above under "General reaction technique 2"). Further strategies to introduce other amine protecting groups have been described in *Protecting Groups in Organic Synthesis*, 3$^{rd}$ Ed (1999), 494-653, T. W. Greene, P.G.M. Wuts (Publisher: John Wiley and Sons, Inc., New York).

General Reaction Technique 6 (Oxidation of an Alcohol into a Ketone or Aldehyde):

The alcohols can be transformed into their corresponding ketones or aldehydes through oxidation under Swern (see D. Swern et al., *J. Org. Chem.* (1978), 43, 2480-2482), Dess-Martin (see D. B. Dess and J. C. Martin, *J. Org. Chem.* (1983), 48, 4155) or Ley (using tetrapropylammonium perruthenate; see *Synthesis* (1994), 7, 639-66) conditions, respectively. Additional methods can be found in *Comprehensive Organic Transformations. A guide to Functional Group Preparations,* 2nd Edition, R. C. Larock, Wiley-VC; New York, Chichester, Weinheim, Brisbane, Singapore, Toronto (1999), Section aldehydes and ketones, p. 1234-1249.

General Reaction Technique 7 (Alcohol Activation):

The alcohol is reacted with MsCl, TfCl or TsCl in presence of a base such as TEA in a dry aprotic solvent such as Pyr, THF or DCM between −30° C. and 50° C. In the case of the triflate or mesylate, Tf$_2$O or Ms$_2$O can also be used. These sulfonates can be reacted with sodium halogenide such as NaI or NaBr in MeCN or DMF between 40° C. and 120° C. delivering the corresponding iodide derivatives. Alternatively the corresponding bromides or chlorides can also be obtained by reaction of the corresponding alcohol derivatives with PBr$_3$ or PCl$_3$ respectively.

General Reaction Technique 8 (Amine Substitution):

The alcohol, activated either as a sulphonate or a iodide derivative (see above under "General reaction technique 7"), is reacted with the amine in presence of an organic base such as TEA or DIPEA in a solvent such as DMF between 20° C. and 110° C.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

The compounds of formula I can be manufactured in accordance with the present invention by a) reducing the compounds of formula II

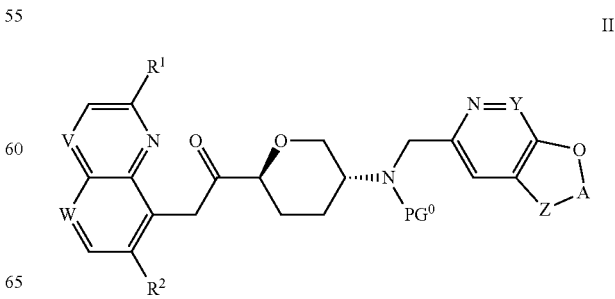

wherein R¹, R², V, W, Y, Z and A are as defined in formula I and PG⁰ represents an amino protecting group such as Cbz, Boc or Fmoc with a hydride reagent such as LiAlH₄, NaBH₄ or NaBD₄ (see general reaction technique 1), the protecting group PG⁰ being then removed following general reaction technique 3; or b) Reacting the Compounds of Formula III

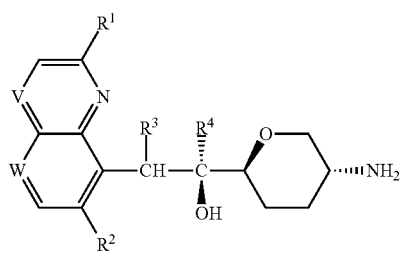

III wherein R¹, R², R³, R⁴, V and W are as defined in formula I with the compounds of formula IV

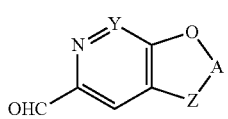

IV wherein A, Y and Z are as in formula I under reductive amination conditions (see general reaction technique 2), whereby, in the particular case wherein R⁵ or R⁶ is D and the other is H, the reaction is performed in the presence of NaBD₄; or c) reacting the compounds of formula III as defined in section b) above with the compounds of formula IVa

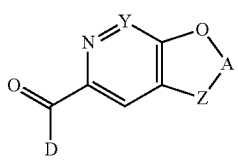

IVa wherein A, Y and Z are as in formula I under reductive amination conditions (see general reaction technique 2), whereby, in the particular case wherein each of R⁵ and R⁶ is D, the reaction is performed in the presence of NaBD₄; or d) reacting the compounds of formula III as defined in section b) above with the compounds of formula V

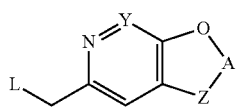

V wherein Y, Z and A are as defined in formula I and L represents a halogen such as chlorine, bromine or iodine or a group of the formula OSO₂Rᵃ wherein Rᵃ represents alkyl, tolyl or trifluoromethyl, following general reaction technique 8; or e) reacting the anion obtained from a compound of formula VI

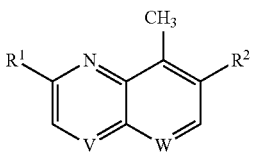

VI wherein R¹, R², V and W are as defined in formula I with the compounds of formula VII

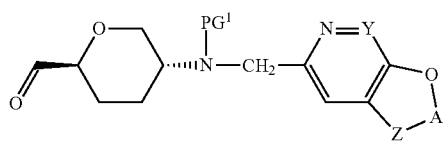

VII wherein Y, Z and A are as defined in formula I and PG¹ is an amino protecting group, whereby the anion is generated with a strong base such as n-BuLi in THF between −50° C. and −100° C. and further reacted with the aldehyde of formula VII between −78° C. and −20° C., the protecting group PG¹ being then removed following general reaction technique 3; or f) reacting the compounds of formula VIII

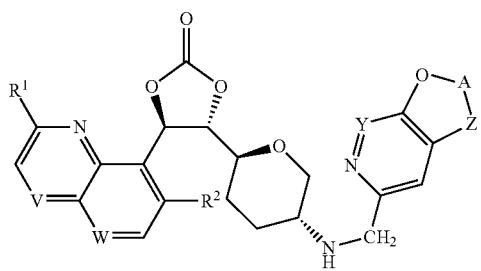

VIII wherein R¹, R², V, W, Y, Z and A are as defined in formula I, with hydrogen over a noble metal catalyst such as Pd/C or with NaBH₄ or NaBD₄ over Pd₂(dba)₃; or g) reacting the anion generated from a compound of formula IX

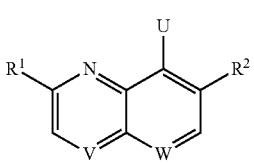

IX wherein R¹, R², V and W are as defined in formula I and U represents a halogen such as bromine or chlorine, with an epoxide of formula X

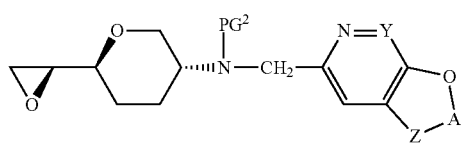

wherein Y, Z and A are as in formula I and $PG^2$ represents an amino protecting group such as Cbz, Boc or Fmoc, whereby the anion is generated by halogen metal exchange with n-BuLi in THF between −50° C. and −100° C., the protecting group $PG^2$ being then removed following general reaction technique 3.

The compounds of formula I thus obtained may, if desired, be converted into their salts, and notably into their pharmaceutically acceptable salts.

Besides, whenever the compounds of formula I are obtained in the form of mixtures of diastereomers, the diastereomers can be separated using methods known to one skilled in the art, e.g. by HPLC over a chiral stationary phase such as a Regis Whelk-Ol(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA or diethylamine) and eluent B (hexane), at a flow rate of 0.8 to 150 mL/min. The mixtures of diastereomers may also be separated by an appropriate combination of silica gel chromatography, HPLC and crystallization techniques.

Preparation of the Compounds of Formulae II to X:

Preparation of the Compounds of Formula II

The compounds of formula II can be prepared as described in Scheme 1 hereafter.

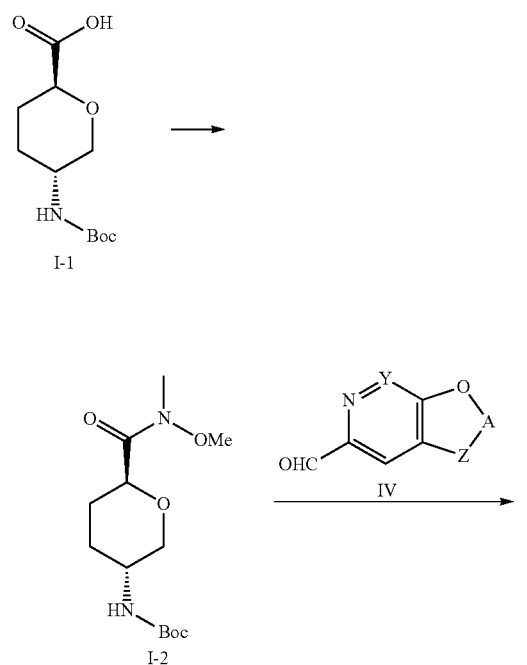

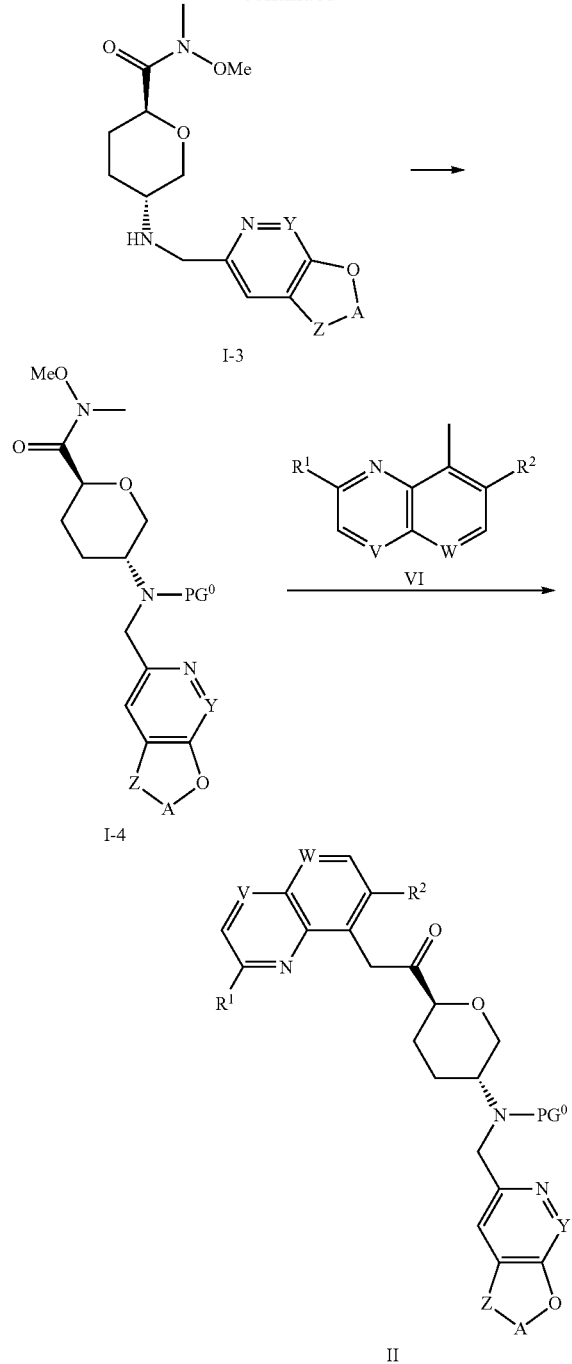

In Scheme 1, $R^1$, V, W, $R^2$, Y, Z and A have the same meaning as in formula I and $PG^0$ is an amino protecting group such as Cbz, Boc or Fmoc.

The known carboxylic acid derivative of formula I-1 (*Eur. J. Org. Chem.* (2003), 2418-27) can be transformed into its corresponding Weinreb amide after reaction with N-methoxy-methanamine in presence of a coupling reagent such as DCC (general reaction technique 4). The Boc protecting group can be removed (general reaction technique 3) and the resulting amine can be reacted with the aldehydes of formula IV (general reaction technique 2). The free amine in the intermediates of formula I-3 can be protected with the group $PG^0$ following general reaction technique 5. The resulting intermediates of formula I-4 can be reacted with the anions generated by the reaction of the derivatives of formula VI with a strong base such as n-BuLi in a solvent such as THF between −30° C. and −100° C., affording the compounds of formula II.

Preparation of the Compounds of Formula III

The compounds of formula III can be obtained by deprotection of the corresponding compounds of formula XI

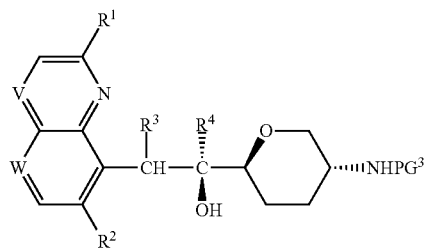

XI wherein $PG^3$ represents an amino protecting group such as Boc, Fmoc or Cbz using general reaction technique 3.

Preparation of the Compounds of Formula IV

The compounds of formula IV wherein A is $CH_2$ or $CH_2CH_2$ can be prepared as described in the literature (see WO 02/056882, WO 2004/058144 and WO 2007/071936). The compounds of formula IV wherein A represents $CD_2CD_2$ can be made in analogy to the compounds wherein A is $CH_2CH_2$ using $BrCD_2CD_2Br$, $HOCD_2CD_2OH$ and $HSCD_2CD_2OH$ respectively.

Preparation of the Compounds of Formula IVa

The compounds of formula IVa can be obtained by reduction of the esters derived from the aldehydes of formula IV (said esters being prepared according to e.g. WO 2007/081597 or WO 2003/087098) with $LiAl D_4$ followed by reoxidation with $MnO_2$.

Preparation of the Compounds of Formula V

The compounds of formula V wherein L represents $OSO_2R^a$ can be obtained by activation of the corresponding alcohol derivatives (L=OH) following general reaction technique 7. The compounds of formula V wherein L represents halogen can be obtained from the former compounds upon reaction with a lithium, potassium or sodium halogenide following general reaction technique 7. The required alcohol derivatives (L=OH and A=$CH_2$ or A=$CH_2CH_2$) can be obtained according to known procedures (e.g. WO 2004/058144) or by reduction of the corresponding aldehyde derivatives of formula IV following general reaction technique 1. The alcohol derivatives wherein A is $CD_2CD_2$ can be obtained by analogy to the aforementioned procedures using appropriate deuterated reaction materials.

Preparation of the Compounds of Formula VI

The compounds of formula VI wherein V is CH, W is CH or wherein W is N and $R^2$ is H can be prepared as described in the literature (see WO 00/21948, WO 2006/046552 and WO 2007/081597).

The compounds of formula VI wherein V is CH, W is N and $R^2$ is F can be prepared as described in Scheme 2 hereafter.

Scheme 2

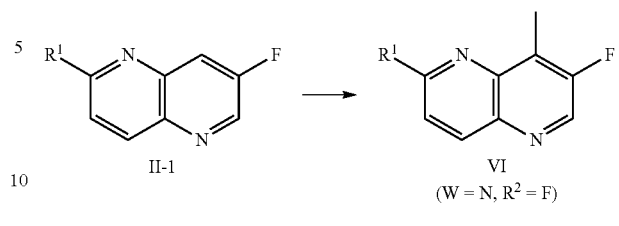

Accordingly, the known compounds of formula II-1 (e.g. $R^1$=OMe; WO 2008/009700) can be reacted with a strong base such as n-BuLi in a solvent such as THF between −30° C. and −100° C., and the resulting anion is quenched with methyl iodide.

The compounds of formula VI wherein V is N, W is CH and $R^2$ is H or F are commercially available or can be prepared as described in the literature (WO 2007/115947).

Preparation of the Compounds of Formula VII

The compounds of formula VII can be prepared as described in Scheme 3 hereafter.

Scheme 3

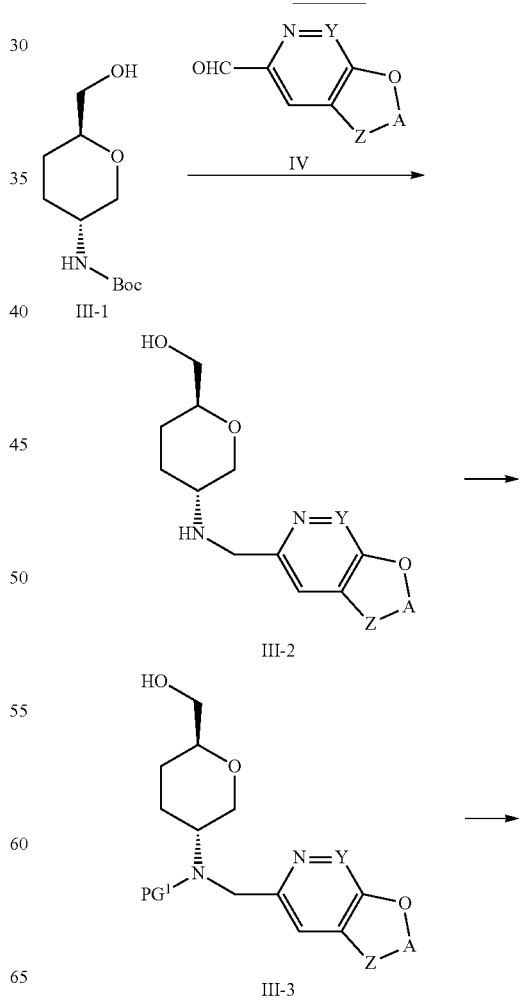

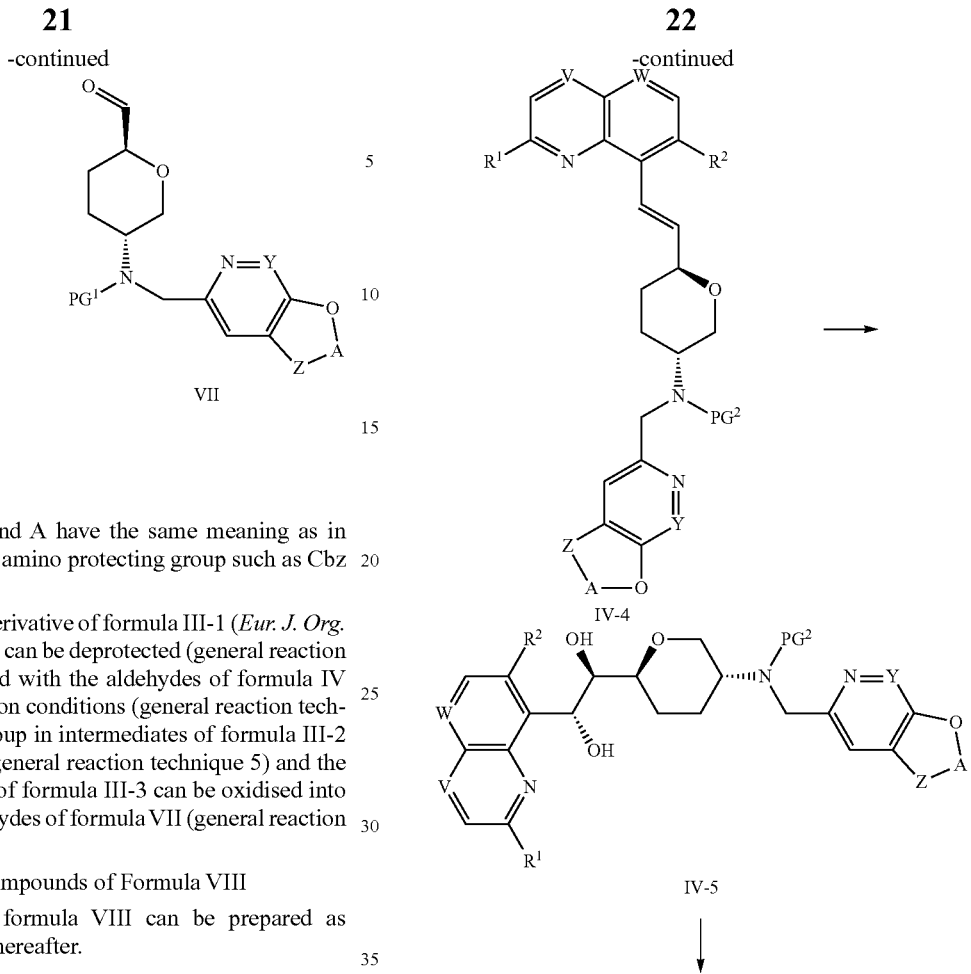

In Scheme 3, Y, Z and A have the same meaning as in formula I and PG$^1$ is an amino protecting group such as Cbz or Boc.

The known alcohol derivative of formula III-1 (*Eur. J. Org. Chem.* (2003), 2418-27) can be deprotected (general reaction technique 3) and reacted with the aldehydes of formula IV under reductive amination conditions (general reaction technique 2). The amino group in intermediates of formula III-2 can then be protected (general reaction technique 5) and the resulting intermediates of formula III-3 can be oxidised into the corresponding aldehydes of formula VII (general reaction technique 6).

Preparation of the Compounds of Formula VIII

The compounds of formula VIII can be prepared as described in Scheme 4 hereafter.

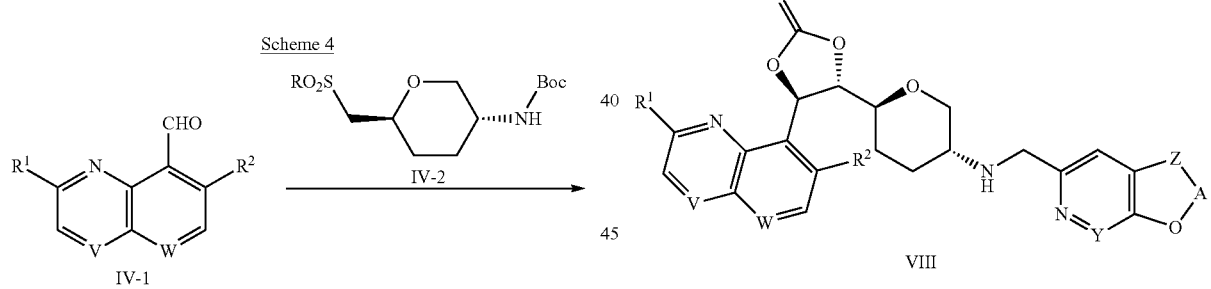

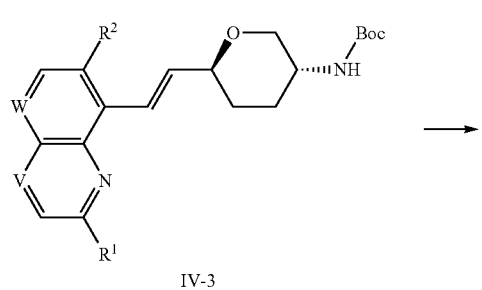

In Scheme 4, R$^1$, R$^2$, V, W, Y, Z and A have the same meaning as in formula I, PG$^2$ is an amino protecting group such as Cbz or Boc and R is 1-phenyl-1H-tetrazol-5-yl or benzothiazol-2-yl.

Accordingly, the sulfones of formula IV-2 (prepared according to WO 2006/032466) and the aldehydes of formula IV-1 can be coupled in presence of a base such as KHMDS or LiHMDS in a solvent such as 1,2-dimethoxyethane, DMF or toluene as reviewed by Blakemore, P. R in *J. Chem. Soc., Perkin Trans.* 1 (2002), 2563-2585. The (E)-alkene derivatives of formula IV-3 can be deprotected (general reaction technique 3) and the resulting free amines can be reacted with the aldehydes of formula IV under reductive amination conditions (general reaction technique 2). The free amines can then be protected (general reaction technique 5), affording the intermediates of formula IV-4. These intermediates can be transformed into the corresponding chiral cis-diol derivatives by treatment with AD-mix β in presence of methanesulfonamide in a water/2-methyl-2-propanol mixture as described in Chem. Rev. (1994), 94, 2483. The chiral cis-diols of formula IV-5 can be transformed into the corresponding cyclic carbonates by treatment either with phosgene, diphosgene or triphosgene in the presence of an organic base such as TEA or Pyr, or with carbonyldimidazole in an inert solvent such as DCM or THF at a temperature ranging between −78° C. and 50° C., more conveniently at a temperature ranging between 0° C. and 20° C. These cyclic carbonates can then be converted into the compounds of formula VIII by removal of the protecting group $PG^2$ (general reaction technique 3). In the particular case wherein $PG^2$ represents Cbz, the hydrogenolysis of the intermediates of formula IV-5 leads directly to the formation of the compounds of formula I.

Preparation of the Compounds of Formula IX

The compounds of formula IX wherein V is CH and W is CH or N are either commercially available or can be obtained according to WO 2008/003690, WO 2006/125974, WO 2006/032466, WO 2005/019215 or WO 2004/058144.

The compounds of formula IX wherein V is N, W is CH and $R^1$ is methoxy can be prepared as described in Scheme 4a hereafter.

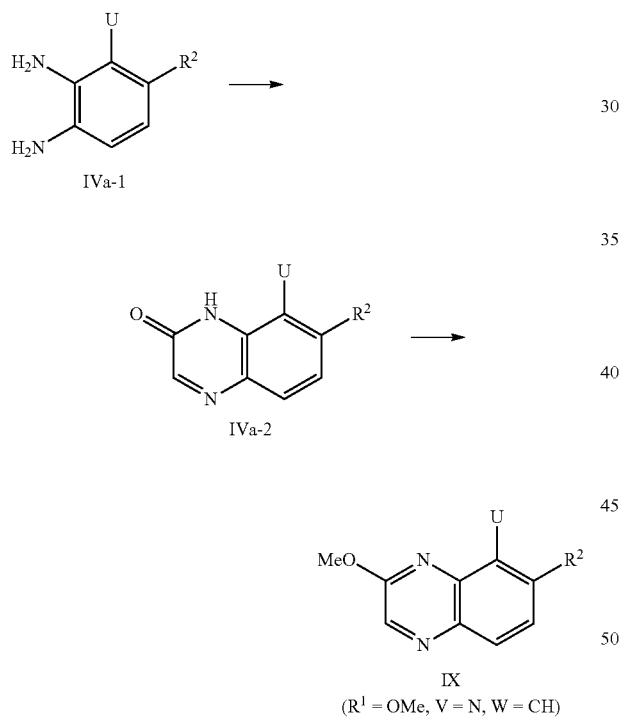

Scheme 4a

Accordingly, the compounds of formula IX wherein V is N, W is CH and $R^1$ is methoxy can be obtained by reacting (for example) 3-chloro-4-fluoro-1,2-benzenediamine (CAS 132915-81-2; commercial) or 3-bromobenzene-1,2-diamine (CAS 1575-36-6; commercial) with methyl glyoxylate. The resulting compounds of formula IV-2 can then be sequentially reacted with $POCl_3$ or $POBr_3$ followed by NaOMe in methanol, affording the compounds of formula IX wherein V is N, W is CH, U is Cl or Br and $R^1$ is methoxy.

Preparation of the Compounds of Formula X

The compounds of formula X can be prepared as described in Scheme 5 hereafter.

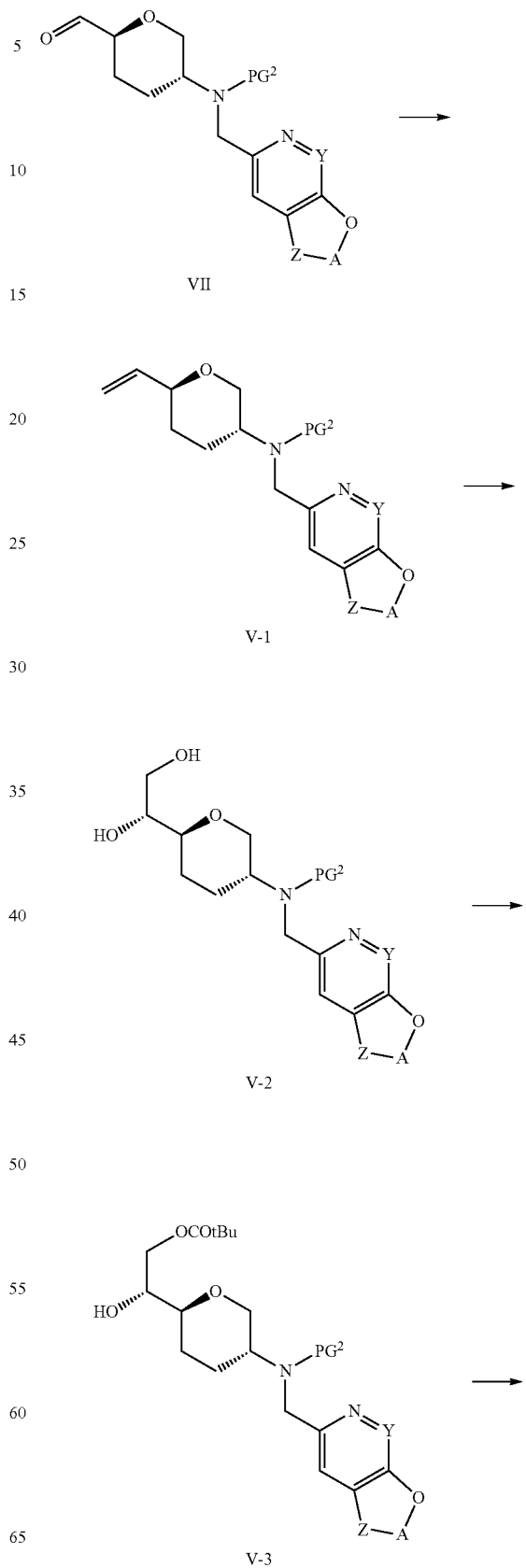

Scheme 5

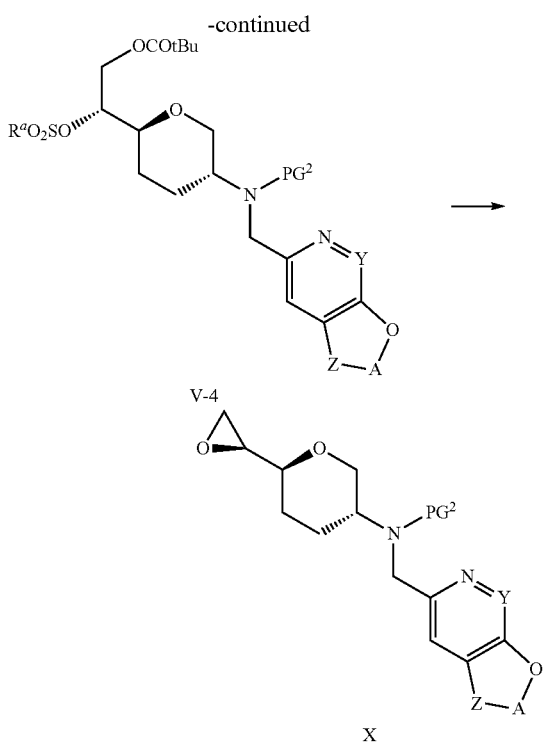

In Scheme 5, Y, Z and A have the same meaning as in formula I, $PG^2$ represents an amino protecting group such as Boc or Cbz and $R^a$ represents alkyl, $CF_3$ or tolyl.

The aldehydes of formula VII can be reacted with methylenetriphenylphosphorane, affording the intermediate vinyl derivatives of formula V-1 which can be subjected to cis-dihydroxylation using AD-mix α. The intermediate diol derivatives of formula V-2 can be monoprotected with a protecting group such as pivaloyl by reaction with pivaloyl chloride in presence of a base such as TEA or DIPEA. The secondary alcohol function can then be activated as a sulphonate (general reaction technique 7) and the epoxides can finally be obtained by reacting the intermediates of formula V-4 with a base such as NaOMe in MeOH.

Preparation of the Compounds of Formula XI:

The compounds of formula XI wherein $R^3$ or $R^4$ represents H can be prepared as described in WO 2006/032466.

The compounds of formula XI wherein one of $R^3$ or $R^4$ is D and the other is H and $PG^3$ is Boc can be prepared as described in Scheme 6 hereafter.

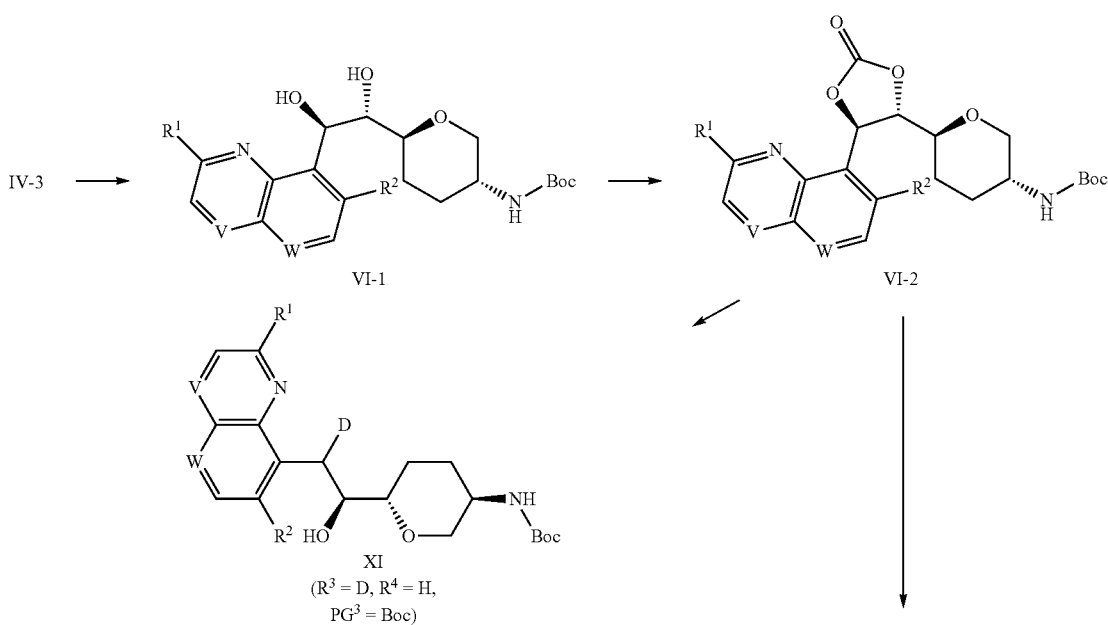

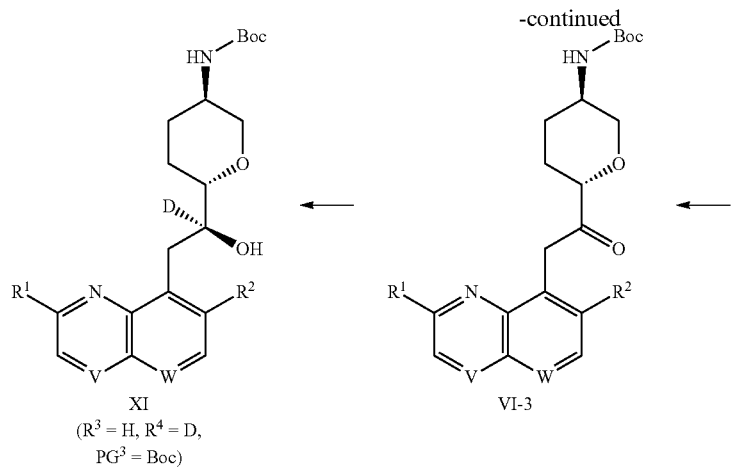
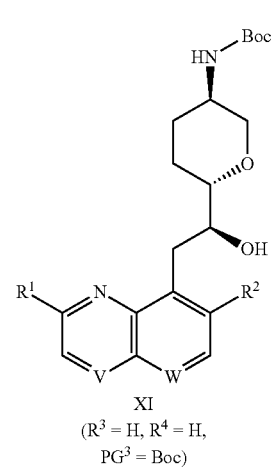

XI
(R³ = H, R⁴ = D,
PG³ = Boc)

VI-3

XI
(R³ = H, R⁴ = H,
PG³ = Boc)

In Scheme 6, $R^1$, $R^2$, V, W and Z have the same meaning as in formula I.

The olefinic derivatives of formula IV-3 can be cis-dihydroxylated by treatment with AD-mix β in presence of methanesulfonamide in a water/2-methyl-2-propanol mixture as described in *Chem. Rev.* (1994), 94, 2483. The chiral cis-diols of formula VI-1 can be transformed into the corresponding cyclic carbonates of formula VI-2 by treatment either with phosgene, diphosgene or triphosgene in the presence of an organic base such as TEA or Pyr, or with carbonyldimidazole in an inert solvent such as DCM or THF at a temperature ranging between −78° C. and 50° C., more conveniently at a temperature ranging between 0° C. and 20° C. These cyclic carbonates can be transformed either into the deutero analogue derivatives of formula XI wherein $R^3$ is D, $R^4$ is H and $PG^3$ is Boc after reaction with $NaBD_4$ in presence of catalysts such as $Pd_2(dba)_3$ or into the analogue derivatives of formula XI wherein $R^3$ is H, $R^4$ is H, and $PG^3$ is Boc after reaction with $NaBH_4$ in presence of catalysts such as $Pd_2(dba)_3$ or through hydrogenation over a noble metal catalyst such as Pd/C. The resulting alcohols derivatives can be oxydized into the corresponding ketone derivatives of formula VI-3 using general reaction technique 6 and further reduced into the corresponding derivatives of formula XI wherein $R^3$ is H, $R^4$ is D and $PG^3$ is Boc with $NaBD_4$.

Particular embodiments of the invention are described in the following Examples, which serve to illustrate the invention in more detail without limiting its scope in any way.

EXAMPLES

In the following section, unless stated otherwise, the "usual aq. work-up" means that after extraction of the aq. layer with an appropriate solvent, the combined org. layers are washed with brine, dried over $Na_2SO_4$, filtered and concentrated to dryness.

All temperatures are stated in ° C. The compounds were characterized by ¹H-NMR (300 MHz) (Varian Oxford); or by ¹H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad, coupling constants are given in Hz. Alternatively the compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$). Unless mentioned otherwise, the compounds were purified by chromatography on Silica gel 60A. $NH_4OH$ as used for CC is 25% aq.

Example 1

(1S)-1-{(2S,5R)-5-[(2,3-dihydro-[1,4]dioxino[2,3-c]pyridin-7-ylmethyl)-amino]tetrahydro-pyran-2-yl}-2-(6-methoxy-[1,5]naphthyridin-4-yl)-ethanol To a solution of (1S)-(2S,5R)-5-amino-tetrahydro-pyran-2-(((6-methoxy-[1,5]naphthyridin-4-yl)-ethanol (0.12 g; 0.4 mmol; prepared according to WO 2006/032466) in MeOH (1.5 mL) and DCE (6 mL) were added 3 Å molecular sieves (1.2 g) and 2,3-dihydro-[1,4]dioxino[2,3-c]pyridine-7-carbaldehyde (0.07 g, 0.4 mmol, prepared according to WO 02/056882). The mixture was stirred at 50° C. overnight. The reaction mixture was cooled to 0° C. and $NaBH_4$ (0.09 g, 2.29 mmol) was added. The reaction proceeded for 1 h at this temperature. The reaction mixture was diluted with DCM-MeOH (9-1, 30 mL) and filtered. The solid was washed with DCM (20 mL). The filtrate was washed with a sat. $NaHCO_3$ solution (10 mL) and the aq. layer was extracted three times by DCM-MeOH (3×10 mL). The org. layer was dried over $Na_2SO_4$, filtered and concentrated to dryness. The residue was purified by CC (DCM-MeOH 93-7 containing 0.7% aq. $NH_4OH$) to afford the title compound as a white foam (0.125 g, 70% yield).

¹H NMR (d6-DMSO) δ: 8.63 (d, J=4.7 Hz, 1H); 8.21 (d, J=9.1 Hz, 1H); 7.99 (s, 1H); 7.50 (d, J=4.4 Hz, 1H); 7.21 (d, J=9.1 Hz, 1H); 6.91 (s, 1H); 4.51 (d, J=6.4 Hz, 1H); 4.30-4.34 (m, 2H); 4.24-4.28 (m, 2H); 3.99 (s, 3H); 3.96 (overlapped m, 1H); 3.85 (m, 1H); 3.68 (AB system, J=14.4 Hz, Δ=0.05 ppm, 2H); 3.42 (dd, J=3.8, 12.9 Hz, 1H); 3.09 (ddd, J=2.1, 3.9, 11.1 Hz, 1H); 2.96 (dd, J=9.0, 12.9 Hz, 1H); 2.91 (t, J=10.5 Hz, 1H); 2.42 (overlapped m, 1H); 2.07 (br. s, 1H); 1.99 (m, 1H); 1.62 (m, 1H); 1.45 (m, 1H); 1.15 (m, 1H).

MS (ESI, m/z): 453.0 [M+H⁺] for $C_{24}H_{28}N_4O_5$.

Example 2

(1S)-1-{(2S,5R)-5-[(6,7-dihydro-[1,4]dioxino[2,3-c]pyridazin-3-ylmethyl)-amino]-tetrahydro-pyran-2-yl}-2-(6-methoxy-[1,5]naphthyridin-4-yl)-ethanol Starting from (1S)-1-((2S,5R)-5-amino-tetrahydro-pyran-2-yl)-2-(6-methoxy-[1,5]naphthyridin-4-yl)-ethanol (0.1 g, 0.33 mmol, prepared according to WO 2006/032466) and 6,7-dihydro-[1,4]dioxino[2,3-c]pyridazine-3-carbaldehyde (0.06 g, 1 eq.; prepared according to WO 2007/071936), and using the procedure of Example 1, the title compound was obtained as a colourless oil (0.008 g, 8% yield). The compound was purified by CC (DCM-MeOH 93-7 containing 0.7% aq. NH$_4$OH).

MS (ESI, m/z): 454.3 [M+H$^+$] for C$_{23}$H$_{27}$N$_5$O$_5$.

Example 3

(1S)-1-{(2S,5R)-5-[(2,3-dihydro-[1,4]dioxino[2,3-c] pyridin-7-ylmethyl)-amino]-tetrahydro-pyran-2-yl}-2-(3-fluoro-6-methoxy-[1,5]naphthyridin-4-yl)-ethanol 3.i. {(3R,6S)-6-[(4R,5R)-5-(3-fluoro-6-methoxy-[1,5]naphthyridin-4-yl)-2-oxo-[1,3]dioxolan-4-yl]-tetrahydro-pyran-3-yl}-carbamic acid tert-butyl ester To an ice-chilled solution of {(3R,-6S)-6-[(1R,2R)-2-(3-fluoro-6-methoxy-[1,5]naphthyridin-4-yl)-1,2-dihydroxyethyl]-tetrahydro-pyran-3-yl}-carbamic acid tert-butyl ester (5.56 g, 12.71 mmol; prepared according to WO 2006/032466) in DCM (115 mL) were added Pyr (6.13 mL, 76.25 mmol) and triphosgene (1.89 g, 6.35 mmol). The reaction mixture was stirred at the same temperature for 25 min and a sat. NaHCO$_3$ solution (100 mL) was added. The two layers were decanted and the aq. layer was extracted with DCM (100 mL). The combined org. layers were washed with brine, dried over Na$_2$SO$_4$, filtered and concentrated to dryness. The residue was co-evaporated twice with toluene to afford the title carbonate as a white solid (4.56 g, 77% yield).

1H NMR (d6-DMSO) δ: 8.93 (d, J=0.9 Hz, 1H); 8.36 (d, J=9.4 Hz, 1H); 7.31 (d, J=9.4 Hz, 1H); 6.77 (d, J=7.6 Hz, 1H); 6.32 (d, J=5.6 Hz, 1H); 5.07 (dd, J=3.2, 5.6 Hz, 1H); 4.01 (s, 3H); 3.93 (m, 1H); 3.54 (m, 1H); 3.35 (m, 1H); 3.08 (t, J=10.5 Hz, 1H); 1.88 (m, 1H); 1.67 (m, 1H); 1.32-1.51 (m, 2H); 1.36 (s, 9H).

MS (ESI, m/z): 464.0 [M+H$^+$] for C$_{22}$H$_{26}$N$_3$O$_7$F.

3.ii. {(3R,6S)-6-[(1S)-2-(3-fluoro-6-methoxy-[1,5]naphthyridin-4-yl)-1-hydroxy-ethyl]-tetrahydro-pyran-3-yl}-carbamic acid tert-butyl ester To a solution of the intermediate 3.i (5.92 g, 12.77 mmol) in a solution of EA (120 mL) and MeOH (15 mL) was added 20% Pd(OH)$_2$/C (moisturized, 5.40 g). The reaction was stirred 5 h under hydrogen atmosphere at 45° C. After cooling to rt, the catalyst was removed by filtration, washed with a mixture of EA-MeOH (9-1, 100 mL). The filtrate was concentrated to dryness and the residue was chromatographed (EA-Hept 4-1 to EA-MeOH 9-1) to afford first the fully reduced compound (0.52 g), and then the title compound as a light grey solid (3.18 g, 59% yield).

MS (ESI, m/z): 422.1 [M+H$^+$] for C$_{21}$H$_{28}$N$_3$O$_5$F.

3.iii. (1S)-1-((2S,5R)-5-amino-tetrahydro-pyran-2-yl)-2-(3-fluoro-6-methoxy-[1,5]naphthyridin-4-yl)-ethanol A solution of the intermediate 3.ii (3.18 g, 7.54 mmol) in TFA (30 mL) was stirred at rt for 20 min. After concentration to dryness, the residue was partitioned between a sat. NaHCO$_3$ solution (50 mL) and DCM-MeOH (9-1, 100 mL). The pH of the aq. layer was adjusted to 12 using 32% aq. NaOH. The aq. layer was extracted five times with the same mixture. The combined org. layers were dried over Na$_2$SO$_4$, filtered and concentrated to dryness to afford the title amine as an off-white solid (1.92 g, 79% yield).

$^1$H NMR (d6-DMSO) δ: 8.72 (d, J=0.6 Hz, 1H); 8.25 (d, J=9.1 Hz, 1H); 7.20 (d, J=9.1 Hz, 1H); 4.53 (d, J=6.2 Hz, 1H); 4.01 (s, 3H); 3.91 (m, 1H); 3.77 (ddd, J=1.8, 4.4, 8.2 Hz, 1H); 3.32 (overlapped m, 1H); 3.05-3.16 (m, 2H); 2.81 (t, J=10.3 Hz, 1H); 2.53 (m, 1H); 1.89 (m, 1H); 1.43-1.68 (m, 2H); 1.32 (br. s, 2H); 1.12 (m, 1H).

MS (ESI, m/z): 322.2 [M+H$^+$] for C$_{16}$H$_{20}$N$_3$O$_3$F.

3.iv. (1S)-1-{(2S,5R)-5-[(2,3-dihydro[1,4]dioxino[2,3-c]pyridin-7-ylmethyl)-amino]-tetrahydro-pyran-2-yl}-2-(3-fluoro-6-methoxy-[1,5]naphthyridin-4-yl)-ethanol Starting from the intermediate 3.iii (0.5 g, 1.55 mmol) and 2,3-dihydro-[1,4]dioxino[2,3-c]pyridine-7-carbaldehyde (0.262 g, 1 eq.) and using the procedure of Example 1, the title compound was obtained after purification by two CC procedures (the product obtained after the first CC with DCM-MeOH 93-7 containing 0.7% aq. NH$_4$OH as eluent being purified by a second CC with EA-MeOH 9-1, then DCM-MeOH 9-1 containing 1% aq. NH$_4$OH as eluents) as a colourless oil (0.477 g, 65% yield).

$^1$H NMR (d6-DMSO) δ: 8.72 (d, J=0.6 Hz, 1H); 8.23 (d, J=9.1 Hz, 1H); 7.99 (s, 1H); 7.19 (d, J=9.1 Hz, 1H); 6.91 (s, 1H); 4.53 (d, J=6.2 Hz, 1H); 4.30-4.34 (m, 2H); 4.24-4.28 (m, 2H); 4.00 (s, 3H); 3.85-3.96 (m, 2H); 3.68 (AB system, J=14.4 Hz, Δ=0.05 ppm, 2H); 3.32 (overlapped m, 1H); 3.07-3.16 (m, 2H); 2.90 (t, J=10.3 Hz, 1H); 2.43 (overlapped m, 1H); 2.16 (br. s, 1H); 1.99 (m, 1H); 1.65 (m, 1H); 1.47 (m, 1H); 1.18 (m, 1H).

MS (ESI, m/z): 471.2 [M+H$^+$] for C$_{24}$H$_{27}$N$_4$O$_5$F.

Example 4

(1S)-1-{(2S,5R)-5-[(6,7-dihydro-[1,4]dioxino[2,3-c]pyridazin-3-ylmethyl)-amino]-tetrahydro-pyran-2-yl}-2-(3-fluoro-6-methoxy-[1,5]naphthyridin-4-yl)-ethanol Starting from (1S)-1-((2S,5R)-5-amino-tetrahydro-pyran-2-yl)-2-(6-methoxy-[1,5]naphthyridin-4-yl)-ethanol (0.053 g, 0.165 mmol; prepared according to WO 2006/032466) and 6,7-dihydro-[1,4]dioxino[2,3-c]pyridazine-3-carbaldehyde (0.028 g, 1 eq.; prepared according to WO 2007/071936), and using the procedure of Example 1, the title compound was obtained as a white foam (0.020 g, 26% yield). The compound was purified by CC (DCM-MeOH 93-7 containing 0.7% aq. NH$_4$OH).

$^1$H NMR (d6-DMSO) δ: 8.72 (s, 1H); 8.25 (d, J=9.1 Hz, 1H); 7.19 (d, J=9.1 Hz, 1H); 7.16 (s, 1H); 4.53 (d, J=6.2 Hz, 1H); 4.46-4.51 (m, 2H); 4.35-4.40 (m, 2H); 4.00 (s, 3H); 3.86-3.96 (m, 2H); 3.83 (br. s, 2H); 3.31 (overlapped m, 1H); 3.06-3.16 (m, 2H); 2.91 (t, J=10.3 Hz, 1H); 2.41 (overlapped m, 1H); 2.21 (br. s, 1H); 2.01 (m, 1H); 1.65 (m, 1H); 1.48 (m, 1H); 1.20 (m, 1H).

MS (ESI, m/z): 472.2 [M+H$^+$] for C$_{23}$H$_{26}$N$_5$O$_5$F.

Example 5

(1S)-1-{(2S,5R)-5-[(2,3-dihydro-[1,4]dioxino[2,3-c]pyridin-7-ylmethyl)-amino]-tetrahydro-pyran-2-yl}-2-(7-fluoro-2-methoxy-quinolin-8-yl)-ethanol 5.i. (E)-{(3R,6S)-6-[2-(7-fluoro-2-methoxy-quinolin-8-yl)-vinyl]-tetrahydro-pyran-3-yl}-carbamic acid tert-butyl ester A mixture of 7-fluoro-2-methoxy-quinoline-8-carbaldehyde (5 g, 24.36 mmol; prepared according to WO 2008/

126024) and (3R,6S)-[6-(1-phenyl-1H-tetrazole-5-sulfonyl-methyl)-tetrahydro-pyran-3-yl]-carbamic acid tert-butyl ester (10.32 g, 24.36 mmol, prepared according to WO 2006/032466) in DME (104 mL) was cooled to −60° C. A solution of LiHMDS (1M in THF, 42 mL) was added drop wise over 30 min. The reaction was stirred 1 hour at this temperature before warming slowly to rt. Water (80 mL) and EA (80 mL) were added. The two layers were decanted and the aq. layer was extracted twice with EA (2×100 mL). The combined org. layers were washed with brine (100 mL), dried over $MgSO_4$ and concentrated to dryness. The residue (10.5 g) was carried on without further purification. The analytical data were obtained by trituration of a small portion of the crude in diethyl ether.

$^1$H NMR (d6-DMSO) δ: 8.24 (d, J=8.8 Hz, 1H); 7.83 (dd, J=6.4, 9.1 Hz, 1H); 7.35 (dd, J=9.1, 10.3 Hz, 1H); 7.30 (dd, J=1.2, 16.7 Hz, 1H); 7.01 (d, J=8.8 Hz, 1H); 6.90 (dd, J=5.6, 16.7 Hz, 1H) 6.79 (m, 1H); 3.99 (s, 3H); 3.84-3.99 (m, 2H); 3.37 (m, 1H); 3.08 (t, J=10.5 Hz, 1H); 1.82-1.95 (m, 2H); 1.42-1.54 (m, 2H); 1.38 (s, 9H).

MS (ESI, m/z): 403.2 [M+H$^+$] for $C_{22}H_{27}N_2O_4F$.

5.ii. {(3R,6S)-6-[(1R,2R)-2-(7-fluoro-2-methoxy-quinolin-8-yl)-1,2-dihydroxy-ethyl]-tetrahydro-pyran-3-yl}-carbamic acid tert-butyl ester To a mixture of the intermediate 5.i (10.5 g, 26 mmol) in 2-methyl-2-propanol (130 mL), water (130 mL) and EA (5 mL) were added successively, at rt, methanesulfonamide (2.5 g) and AD-mix β (36 g). Sodium bisulfite (39 g) was added portion-wise to the reaction mixture. The two layers were separated and the aq. layer was extracted with EA (2×150 mL). The combined org. layers were washed with brine, dried over $Na_2SO_4$, filtered and concentrated to dryness. The residue was purified by CC (DCM-MeOH 19:1) to afford the title diol as an off-white foam (9.0 g, 20.6 mmol).

MS (ESI, m/z): 437.0 [M+H$^+$] for $C_{22}H_{29}N_2O_6F$.

5.iii. {(3R,6S)-6-[(4R,5R)-5-(7-fluoro-2-methoxy-quinolin-8-yl)-2-oxo-[1,3]dioxolan-4-yl]-tetrahydro-pyran-3-yl}-carbamic acid tert-butyl ester Starting from intermediate 5.ii (9.0 g 20.6 mml) and triphosgene (3.06 g) and using the procedure of Example 3, step 3.i., the title compound was obtained as a white foam (7.0 g, 73% yield).

MS (ESI, m/z): 463.1 [M+H$^+$] for $C_{23}H_{27}N_2O_7F$.

5.iv. {(3R,6S)-6-[(1S)-2-(7-fluoro-2-methoxy-quinolin-8-yl)-1-hydroxy-ethyl]-tetrahydro-pyran-3-yl}-carbamic acid tert-butyl ester To a solution of the intermediate 5.iii (0.86 g, 1.86 mmol) in EtOH (16 mL) was added ammonium formate (0.56 g, 9.29 mmol) 5% Pd/CaCO$_3$ (0.08 g) and 10% Pd/C (0.004 g). The reaction proceeded for 2 h at rt. The catalysts were removed by filtration, and concentrated in vacuo. Water (15 mL) was added and the mixture was extracted with EA (2×10 mL). The combined org. layer was dried over $Na_2SO_4$, filtered and concentrated to dryness. The residue was purified by CC (EA-Hept 1-2 to 1-1) to afford the title compound as a white foam (0.580 g, 74% yield).

$^1$H NMR (d6-DMSO) δ: 8.21 (d, J=9.1 Hz, 1H); 7.77 (dd, J=6.2, 8.8 Hz, 1H); 7.26 (t, J=9.1 Hz, 1H); 6.95 (d, J=8.8 Hz, 1H); 6.68 (m, 1H); 4.39 (d, J=6.2 Hz, 1H); 3.99 (s, 3H); 3.78-3.90 (m, 2H); 3.27-3.39 (m, 2H) 3.01-3.12 (m, 2H); 2.92 (t, J=10.5 Hz, 1H); 1.88 (m, 1H); 1.48-1.68 (m, 2H); 1.36 (s, 9H), 1.32 (m, 1H).

MS (ESI, m/z): [M+H$^+$] for $C_{22}H_{29}N_2O_5F$.

5.v. (1S)-1-((2S,5R)-5-amino-tetrahydro-pyran-2-yl)-2-(7-fluoro-2-methoxy-quinolin-8-yl)-ethanol Starting from the intermediate 5.iv (0.577 g, 1.37 mmol) and using the procedure described in Example 1, the title amine was obtained as a beige foam (0.441 g, 100% yield).

MS (ESI, m/z): 321.2 [M+H$^+$] for $C_{17}H_{21}N_2O_3F$.

5. vi. (1S)-1-{(2S,5R)-5-[(2,3-dihydro[1,4]dioxino[2,3-c]pyridin-7-ylmethyl)-amino]-tetrahydro-pyran-2-yl}-2-(7-fluoro-2-methoxy-quinolin-8-yl)-ethanol Starting from the intermediate 5.v (0.15 g, 1.55 mmol) and 2,3-dihydro-[1,4]dioxino[2,3-c]pyridine-7-carbaldehyde (0.078 g, 1 eq.) and using the procedure of Example 1, the title compound was obtained after purification by two CC procedures (the product obtained after the first CC with DCM-MeOH 93-7 containing 0.7% aq. NH$_4$OH as eluent being purified by a second CC with EA-MeOH 9-1, then DCM-MeOH 9-1 containing 1% aq. NH$_4$OH as eluents) as a colourless oil (0.068 g, 31% yield).

$^1$H NMR (d6-DMSO) δ: 8.20 (d, J=8.8 Hz, 1H); 7.99 (s, 1H); 7.76 (dd, J=6.4, 9.1 Hz, 1H); 7.25 (t, J=9.1 Hz, 1H); 6.95 (d, J=8.8 Hz, 1H); 6.91 (s, 1H); 4.29-4.35 (m, 3H); 4.23-4.28 (m, 2H); 3.97 (s, 3H); 3.95 (overlapped m, 1H); 3.84 (m, 1H); 3.68 (AB system, J=14.4 Hz, Δ=0.05 ppm, 2H); 3.31 (overlapped m, 1H); 3.02-3.13 (m, 2H); 2.90 (t, J=10.3 Hz, 1H); 2.44 (overlapped m, 1H); 1.95-2.10 (m, 2H); 1.61 (m, 1H); 1.48 (m, 1H); 1.18 (m, 1H).

MS (ESI, m/z): 470.1 [M+H$^+$] for $C_{25}H_{28}N_3O_5F$.

Example 6

(1S)-1-{(2S,5R)-5-[(2,3-dihydro-4-oxa-1-thia-6-aza-naphthalen-7-ylmethyl)-amino]-tetrahydro-pyran-2-yl}-2-(3-fluoro-6-methoxy-[1,5]naphthyridin-4-yl)-ethanol

6.i. Methanesulfonic acid 2,3-dihydro-4-oxa-1-thia-6-aza-naphthalen-7-ylmethyl ester To a suspension of (2,3-dihydro-4-oxa1-thia-6-aza-naphthalen-7-yl)-methanol (0.150 g, 0.8 mmol; prepared as described in WO 2004/058144) in DCM (4 mL), cooled to 0° C., were added TEA (0.228 mL, 1.6 mmol, 2 eq.) and MsCl (0.076 mL, 0.98 mmol, 1.2 eq.). The reaction was stirred at the same temperature. MsCl (0.013 mL, 0.16 mmol) was added after 30 min. A sat. NaHCO$_3$ solution (25 mL) and DCM (20 mL) were added. The two layers were decanted and the org. layer was dried over Na$_2$SO$_4$, filtered and concentrated to dryness. The residue was purified by CC (DCM-MeOH 97-3) to afford the tittle compound as a yellowish oil (0.210 g, 98% yield).

MS (ESI, m/z): 262.0 [M+H$^+$] for $C_9H_{11}NO_4S_2$.

6.ii. (1S)-1-{(2S,5R)-5-[(2,3-dihydro-4-oxa-1-thia-6-aza-naphthalen-7-ylmethyl)-amino]-tetrahydro-pyran-2-yl}-2-(3-fluoro-6-methoxy-[1,5]naphthyridin-4-yl)-ethanol To a solution of intermediate 3.iii (0.08 g, 0.25 mmol) and intermediate 6.i (0.065 g, 0.25 mmol) in DMF (1.5 mL) was added DIPEA (0.104 mL, 0.625 mmol). The mixture was heated to 80° C. overnight. The solvent was removed under reduced pressure and the residue was filtered through hydromatrix® (pretreated with a sat. NaHCO$_3$ solution) using DCM-MeOH (9-1) as eluent. The filtrate was concentrated to dryness and the residue was purified by CC (DCM-MeOH 19-1 containing 0.5% aq. NH$_4$OH) to afford the title compound as a beige foam (0.045 g, 37% yield).

$^1$H NMR (d6-DMSO) δ: 8.72 (d, J=0.6Hz, 1H); 8.25 (d, J=9.1 Hz, 1H); 7.92 (s, 1H); 7.19 (d, J=9.1 Hz, 1H); 7.13 (s, 1H); 4.53 (d, J=5.9 Hz, 1H); 4.33-4.37 (m, 2H); 4.00 (s, 3H); 3.84-3.97 (m, 2H); 3.68 (AB system, J=14.4 Hz, Δ=0.05 ppm, 2H); 3.31 (overlapped m, 1H); 3.22-3.26 (m, 2H); 3.06-3.16 (m, 2H); 2.90 (t, J=10.5 Hz, 1H); 2.43 (overlapped m, 1H); 1.96-2.08 (m, 2H); 1.65 (m, 1H); 1.48 (m, 1H); 1.19 (m, 1H).

MS (ESI, m/z): 487.3 [M+H$^+$] for C$_{24}$H$_{27}$N$_4$O$_4$FS.

Example 7

(1S)-1-{(2S,5R)-5-[(2,3-dihydro-4-oxa-1-thia-6-aza-naphthalen-7-ylmethyl)-amino]-tetrahydro-pyran-2-yl}-2-(7-fluoro-2-methoxy-quinolin-8-yl)-ethanol Starting from intermediate 5.v (0.08 g, 0.25 mmol) and intermediate 6.i (0.065 g, 0.25 mmol) the title compound was obtained as a beige foam (0.040 g, 85% purity). The crude reaction mixture was purified by CC (DCM-MeOH 19-1 containing 0.5% aq. NH$_4$OH).

MS (ESI, m/z): 486.1 [M+H$^+$] for C$_{25}$H$_{28}$N$_3$O$_4$FS.

Example 8

(1S)-2-(3-fluoro-6-methoxy-[1,5]naphthyridin-4-yl)-1-{(2S,5R)-5-[(3-oxa-1-thia-5-aza-indan-6-ylmethyl)-amino]tetrahydro-pyran-2-yl}-ethanol 8.i. Methanesulfonic acid 3-oxa-1-thia-5-aza-indan-6-ylmethyl ester Starting from (3-oxa-1-thia-5-aza-indan-6-yl)-methanol (prepared as described in WO 2004/058144; 0.450 g, 2.66 mmol); the title mesylate was obtained as a purple oil (0.468 g, 71% yield) using the procedure of Example 6, step 6.i.

$^1$H NMR (d6-DMSO) δ: 8.07 (s, 1H); 7.54 (s, 1H); 5.87 (s, 2H); 5.15 (s, 2H); 3.31 (s, 3H).

MS (ESI, m/z): 248.0 [M+H$^+$] for C$_8$H$_9$NO$_4$S$_2$.

8.ii. (1S)-2-(3-fluoro-6-methoxy-[1,5]naphthyridin-4-yl)-1-{(2S,5R)-5-[(3-oxa-1-thia-5-aza-indan-6-ylmethyl)-amino]-tetrahydro-pyran-2-yl}-ethanol Starting from the intermediate 3.iii (0.08 g, 0.25 mmol) and the intermediate 8.i (0.061 g, 0.25 mmol), the title compound was a obtained as a beige foam (0.030 g, 25% yield) using the procedure of Example 6, step 6.ii. The crude reaction mixture was purified by CC (DCM-MeOH 97-3 containing 0.3% aq. NH$_4$OH).

$^1$H NMR (d6-DMSO) δ: 8.72 (d, J=0.6 Hz, 1H); 8.25 (d, J=9.1 Hz, 1H); 7.97 (s, 1H); 7.41 (s, 1H); 7.20 (d, J=9.1 Hz, 1H); 5.80 (s, 2H); 4.55 (d, J=6.2 Hz, 1H); 4.00 (s, 3H); 3.84-3.98 (m, 2H); 3.71 (AB system, J=14.4 Hz, Δ=0.05 ppm, 2H); 3.31 (overlapped m, 1H); 3.06-3.16 (m, 2H); 2.90 (t, J=10.5 Hz, 1H); 2.43 (overlapped m, 1H); 2.11 (m, 1H); 2.01 (m, 1H); 1.65 (m, 1H); 1.48 (m, 1H); 1.20 (m, 1H).

MS (ESI, m/z): 487.3 [M+H$^+$] for C$_{24}$H$_{27}$N$_4$O$_4$FS.

Example 9

(1S)-2-(7-fluoro-2-methoxy-quinolin-8-yl)-1-{(2S, 5R)-5-[(3-oxa-1-thia-5-aza-indan-6-ylmethyl)-amino]-tetrahydro-pyran-2-yl}-ethanol Starting from intermediate 5.v (0.085 g, 0.265 mmol) and intermediate 8.i (0.065 g, 0.265 mmol), the title compound was obtained as a beige foam (0.035 g, 35% yield). The crude reaction mixture was purified by CC (DCM-MeOH 97-3 containing 0.3% aq. NH$_4$OH).

MS (ESI, m/z): 472.4 [M+H$^+$] for C$_{25}$H$_{28}$N$_3$O$_4$FS.

Example 10

(1S)-1-{(2S,5R)-5-[(3,4-dihydro-2H-pyrano[2,3-c]pyridin-6-ylmethyl)-amino]-tetrahydro-pyran-2-yl}-2-(3-fluoro-6-methoxy-[1,5]naphthyridin-4-yl)-ethanol 10.i. 6-chloromethyl-3,4-dihydro-2H-pyrano[2,3-c]pyridine Starting from (3,4-dihydro-2H-pyrano[2,3-c]pyridin-6-yl)-methanol (prepared as described in WO 2004/058144; 0.7 g, 4.27 mmol), the title chloride was obtained as a brown solid (0.205 g, 26% yield) using the procedure described in Example 6, step 6.i (during the course of the mesylation reaction subsequent chloride formation took place).

$^1$H NMR (CDCl$_3$) δ: 8.10 (s, 1H); 7.13 (s, 1H); 4.60 (s, 2H); 4.21-4.25 (m, 2H); 2.76-2.82 (m, 2H); 1.99-2.07 (m, 2H).

MS (ESI, m/z): 1842.4 [M+H$^+$] for C$_9$H$_{10}$NOCl.

10.ii. (1S)-1-{(2S,5R)-5-[(3,4-dihydro-2H-pyrano[2,3-c]pyridin-6-ylmethyl)-amino]-tetrahydro-pyran-2-yl}-2-(3-fluoro-6-methoxy-[1,5]naphthyridin-4-yl)-ethanol Starting from intermediate 3.iii (0.08 g, 0.25 mmol) and intermediate 10.i (0.050 g, 0.27 mmol), the title compound was obtained as a beige foam (0.015 g, 13% yield) using the procedure of Example 6, step 6.ii. The crude reaction mixture was purified by CC (DCM-MeOH 97-3 containing 0.3% aq. NH$_4$OH).

$^1$H NMR (d6-DMSO) δ: 8.72 (d, J=0.6 Hz, 1H); 8.25 (d, J=9.1 Hz, 1H); 7.93 (s, 1H); 7.20 (d, J=9.1 Hz, 1H); 7.08 (s, 1H); 4.55 (d, J=6.2 Hz, 1H); 4.12-4.17 (m, 2H); 4.00 (s, 3H); 3.86-3.99 (m, 2H); 3.70 (AB system, J=14.4 Hz, Δ=0.05 ppm, 2H); 3.32 (overlapped m, 1H); 3.06-3.16 (m, 2H); 2.91 (t, J=10.3 Hz, 1H); 2.69-2.75 (m, 2H); 2.43 (overlapped m, 1H); 1.86-2.08 (m, 4H); 1.66 (m, 1H); 1.47 (m, 1H); 1.18 (m, 1H).

MS (ESI, m/z): 469.0 [M+H$^+$] for C$_{25}$H$_{29}$N$_4$O$_4$F.

Example 11

(1S)-1-{(2S,5R)-5-[(6,7-dihydro-8-oxa-5-thia-1,2-diaza-naphthalen-3-ylmethyl)-amino]-tetrahydro-pyran-2-yl}-2-(3-fluoro-6-methoxy-[1,5]naphthyridin-4-yl)-ethanol To a solution of 6,7-dihydro-8-oxa-5-thia-1,2-diaza-naphthalene-3-carbaldehyde (0.502 g, 80% purity, 2.2 mmol) in MeOH (15 mL), warmed to 45° C. was added intermediate 3.ii (0.706 g, 2.2 mmol, 1 eq.). The mixture was stirred at 45° C. for 5 min. The solution was let under stirring at rt for 3 h. The mixture was cooled to 0° C. and NaBH$_4$ (0.260 g) was added in one portion. DCM (5 mL) was added and the reaction proceeded for 1 h at the same temperature. The reaction was diluted with DCM (100 mL) and sat. NaHCO$_3$ (30 mL). The two layers were decanted and the aq. layer was extracted once with DCM-MeOH (9-1, 50 mL). The combined org. layers were washed with brine, dried over Na$_2$SO$_4$, filtered and concentrated to dryness. The residue was purified by CC (DCM-MeOH 9-1 containing 1% aq. NH$_4$OH) to afford a white foam. The solid was recrystallized in hot 2-propanol to give the title compound as a white solid (0.43 g).

$^1$H NMR (d6-DMSO) δ: 8.72 (s, 1H); 8.25 (d, J=9.1 Hz, 1H); 7.53 (s, 1H); 7.19 (d, J=9.1 Hz, 1H); 4.51-4.59 (m, 3H); 4.00 (s, 3H); 3.85-3.96 (m, 2H); 3.81 (br. s, 2H); 3.24-3.35 (m, 3H); 3.05-3.16 (m, 2H); 2.90 (t, J=10.3 Hz, 1H); 2.42 (overlapped m, 1H); 2.21 (br. s, 1H); 2.01 (m, 1H); 1.65 (m, 1H); 1.49 (m, 1H); 1.18 (m, 1H).

MS (ESI, m/z): 488.7 [M+H$^+$] for C$_{23}$H$_{26}$N$_5$O$_4$FS.

Example 12

(1S)-1-{(2S,5R)-5-[(2,3-dihydro-[1,4]dioxino[2,3-c]pyridin-7-ylmethyl)-amino]-tetrahydro-pyran-2-yl}-2-(6-fluoro-3-methoxy-quinoxalin-5-yl)-ethanol

12.i. 2-chloro-6fluoro-3-methoxy-quinoxaline-5-carbaldehyde

To a solution of DIPA (22.3 mL) in THF (150 mL) was added at −20° C., n-BuLi (2.3M, 63.7 mL, 159 mmol). The mixture was stirred at −20° C. for 10 min. After cooling to −78° C., a solution of 2-chloro-6-fluoro-3-methoxy-quinoxaline (27.1 g, 127.4 mmol) in THF (100 mL+10 mL rinse) was added over 40 min. The reddish mixture was stirred at −78° C. for 40 min. DMF (15 mL) was added keeping the internal temperature below −70° C. The reaction proceeded 20 min. AcOH (15 mL) was added. Once the mixture had warmed up to rt, 3M HCl (180 mL) and EA (500 mL) were added. The mixture was further diluted with EA (400 mL) until two clear layers were obtained. The two layers were separated and the aq. layer was extracted with EA (3×300 mL). The org. layer was washed twice with sat. aq. NaHCO$_3$ (200 mL) and brine (200 mL), dried over MgSO$_4$, filtered and concentrated to dryness. The crude product was triturated with an ether-EA mixture (1-1, 250 mL), washed with ether (2×100 mL), and dried under high vacuum to afford the title aldehyde as a beige solid (23 g, 76% yield).

$^1$H NMR (d6-DMSO) δ: 10.96 (dd, J=0.9, 1.5 Hz, 1H); 8.29 (dd, J=5.6, 9.4 Hz, 1H); 7.67 (ddd, J=0.6, 9.1, 10.5 Hz, 1H), 4.17 (s, 3H).

12.ii. 6-fluoro-3-methoxy-quinoxaline-5-carbaldehyde

Intermediate 12.i (23 g, 95.6 mmol) was suspended in THF (750 mL) and TEA (26.6 mL) was added. The resulting clear solution was treated with 10% Pd/C (5 g) and stirred under hydrogen atmosphere for 75 min. The reaction mixture was filtered through Celite, water (100 mL) being used to rinse the solids. The two layers were extracted with EA (2×200 mL). The combined org. layers were dried over MgSO$_4$, filtered and concentrated to dryness. The residue was triturated in ether and the solids were filtered off and dried under high vacuum to afford the title compound as a beige solid (16.6 g, 84% yield).

$^1$H NMR (d6-DMSO) δ: 11.15 (dd, J=0.6, 1.5 Hz, 1H); 8.24 (dd, J=5.6, 9.4 Hz, 1H); 7.38 (ddd, J=0.6, 9.4, 10 Hz, 1H); 4.14 (s, 3H).

12.iii. (1S)-1-((2S,5R)-5-amino-tetrahydro-pyran-2-yl)-2-(6-fluoro-3-methoxy-quinoxalin-5-yl)-ethanol Starting from intermediate 12.ii. (3.02 g, 14.64 mmol) and (3R,6S)-[6-(1-phenyl-1H-tetrazole-5-sulfonylmethyl)-tetrahydro-pyran-3-yl]-carbamic acid tent-butyl ester (6.20 g, 14.64 mmol, prepared according to WO 2006/032466), the title amine was obtained as a white solid (1.53 g, 4.76 mmol) using sequentially the procedures of Example 5, steps 5.i (Julia coupling, 58% yield, MS (ESI, m/z): 404.3 [M+H$^+$] for C$_{21}$H$_{26}$N$_3$O$_4$F) and 5.ii (asymmetric dihydroxylation, >100% yield, MS (ESI, m/z): 438.3 [M+H$^+$] for C$_{21}$H$_{28}$N$_3$O$_6$F), of Example 3, step 3.i (carbonate formation, 64% yield, MS (ESI, m/z): 438.3 [M+H$^+$] for C$_{22}$H$_{26}$N$_3$O$_7$F), of Example 5, step 5.iv (hydrogenolysis, 65% yield, MS (ESI, m/z): 422.3 [M+H$^+$] for C$_{21}$H$_{28}$N$_3$O$_5$F) and of Example 3, step 3.ii (Boc deprotection, 78% yield). If necessary, the crude intermediates were purified by CC using an appropriate eluent system.

$^1$H NMR (d6-DMSO) δ: 8.54 (s, 1H); 7.89 (dd, J=5.9, 9.1 Hz, 1H); 7.47 (t, J=9.1 Hz, 1H); 4.38 (d, J=6.2 Hz, 1H); 4.03 (s, 3H); 3.75-3.85 (m, 2H); 3.29 (overlapped m, 1H); 3.00-3.13 (m, 2H); 2.80 (t, J=10.3 Hz, 1H); 2.55 (m, 1H); 1.88 (m, 1H); 1.44-1.65 (m, 2H); 1.30 (br. s, 2H); 1.11 (m, 1H).

MS (ESI, m/z): 322.4 [M+H$^+$] for C$_{16}$H$_{20}$N$_3$O$_3$F

12.iv. (1S)-1-{(2S,5R)-5-[(2,3-dihydro[1,4]dioxino[2,3-c]pyridin-7-ylmethyl)-amino]-tetrahydro-pyran-2-yl}-2-(6-fluoro-3-methoxy-quinoxalin-5-yl)-ethanol Starting from intermediate 12.iii (0.065 g, 0.22 mmol) and 2,3-dihydro-[1,4]dioxino[2,3-c]pyridine-7-carbaldehyde (0.035 g, 1 eq.) and using the procedure of Example 1, the title compound was obtained after purification by CC (DCM-MeOH 93-7 containing 0.7% aq. NH$_4$OH as eluent) as a colourless oil (0.04 g, 40% yield).

$^1$H NMR (d6-DMSO) δ: 8.53 (s, 1H); 7.98 (s, 1H); 7.89 (dd, J=5.6, 9.1 Hz, 1H); 6.91 (s, 1H); 4.38 (d, J=6.2 Hz, 1H); 4.29-4.34 (m, 2H); 4.23-4.28 (m, 2H); 4.03 (s, 3H); 3.93 (m, 1H); 3.79 (m, 1H); 3.65 (AB system, J=14.4 Hz, Δ=0.05 ppm, 2H); 3.29 (overlapped m, 1H); 3.03-3.13 (m, 2H); 2.88 (t, J=10.5 Hz, 1H); 2.42 (overlapped m, 1H); 1.95-2.06 (m, 2H); 1.62 (m, 1H); 1.48 (m, 1H); 1.17 (m, 1H).

MS (ESI, m/z): 471.2 [M+H$^+$] for C$_{24}$H$_{27}$N$_4$O$_5$F.

Example 13

(1S)-1-{(2S,5R)-5-[(6,7-dihydro-[1,4]dioxino[2,3-c]pyridazin-3-ylmethyl)-amino]tetrahydro-pyran-2-yl}-2-(6-fluoro-3-methoxy-quinoxalin-5-yl)-ethanol Starting from intermediate 12.iii (0.296 g, 0.9223 mmol) and 6,7-dihydro-[1,4]dioxino[2,3-c]pyridazine-3-carbaldehyde (0.153 g, 1 eq.) and using the procedure of Example 1, the title compound was obtained as a white foam (0.122 g, 28% yield). The compound was purified by CC (DCM-MeOH 93-7 containing 0.7% aq. NH$_4$OH).

$^1$H NMR (d6-DMSO) δ: 8.53 (s, 1H); 7.88 (dd, J=5.9, 9.1 Hz, 1H); 7.46 (t, J=9.1 Hz, 1H); 7.16 (s, 1H); 4.47-4.50 (m, 2H); 4.35-4.40 (m, 3H); 4.06 (s, 3H); 3.93 (m, 1H); 3.75-3.84 (m, 3H); 3.27 (overlapped m, 1H); 3.03-3.12 (m, 2H); 2.88 (t, J=10.3 Hz, 1H); 2.43 (overlapped m, 1H); 2.25 (br. s, 1H); 2.00 (m, 1H); 1.61 (m, 1H); 1.47 (m, 1H); 1.18 (m, 1H).

MS (ESI, m/z): 472.2 [M+H$^+$] for C$_{23}$H$_{26}$N$_5$O$_5$F.

Example 14

(1S)-1-{(2S,5R)-5-[(2,3-dihydro-4-oxa-1-thia-6-aza-naphthalen-7-ylmethyl)-amino]-tetrahydro-pyran-2-yl}-2-(6-fluoro-3-methoxy-quinoxalin-5-yl)-ethanol Starting from intermediate 12.iii (57 mg, 0.177 mmol) and 2,3-dihydro-[1,4]oxathiino[2,3-c]pyridine-7-carbaldehyde (33 mg, 1 eq.) and using the procedure of Example 1, the title compound was obtained as a white foam (27 mg, 31% yield). The compound was purified by CC (DCM-MeOH 93-7 containing 0.7% aq. NH$_4$OH).

MS (ESI, m/z): 487.2 [M+H$^+$] for $C_{24}H_{27}N_4O_4FS$.

Example 15

(1S)-1-{(2S,5R)-5-[(6,7-dihydro-8-oxa-5-thia-1,2-diaza-naphthalen-3-ylmethyl)-amino]-tetrahydro-pyran-2-yl}-2-(6-fluoro-3-methoxy-quinoxalin-5-yl)-ethanol To a solution of intermediate 12.iii (1.01 g, 3.14 mmol) in MeOH (19.5 mL), heated to 50° C. was added 6,7-dihydro-8-oxa-5-thia-1,2-diaza-naphthalene-3-carbaldehyde (0.57 g, 3.14 mmol, 1 eq.). The mixture was stirred at rt overnight. The reaction mixture was cooled to 0° C. and NaBH$_4$ (0.18 g, 4.71 mmol, 1.5 eq.) was added. After 30 min more NaBH$_4$ (0.06 g, 2.36 mmol, 0.75 eq.) was added. Sat. aq. NaHCO$_3$ (20 mL) was added. The solvent was removed in vacuo until no more volatiles distilled off. DCM-MeOH (9-1, 50 mL) was then added. The two layers were decanted and the aq. layer was extracted twice with DCM-MeOH (9-1, 2×20 mL). The combined org. layers were washed with brine, dried over Na$_2$SO$_4$, filtered and concentrated to dryness. The solid was purified by CC (EA-MeOH 9-1 then DCM-MeOH 19-1 containing 0.5% aq. NH$_4$OH to DCM-MeOH 93-7 containing 0.7% NH$_4$OH) to afford the title compound as a white foam (0.9 g).

$^1$H NMR (d6-DMSO) δ: 8.53 (s, 1H); 7.89 (dd, J=5.9, 9.1 Hz, 1H); 7.53 (s, 1H); 7.46 (t, J=9.1 Hz, 1H); 4.54-4.59 (m, 2H); 4.39 (d, J=6.2 Hz, 1H); 4.03 (s, 3H); 3.93 (m, 1H); 3.75-3.84 (m, 3H); 3.25-3.32 (m, 3H); 3.03-3.12 (m, 2H); 2.88 (t, J=10.3 Hz, 1H); 2.42 (overlapped m, 1H); 2.24 (m, 1H); 2.00 (m, 1H); 1.62 (m, 1H); 1.48 (m, 1H); 1.16 (m, 1H).

MS (ESI, m/z): 488.7 [M+H$^+$] for $C_{23}H_{26}N_5O_4FS$.

Example 16

(1S)-1-((2S,5R)-5-(((2,3-dihydro-[1,4]dioxino[2,3-c]pyridin-7-yl)methyl-d1)amino)tetrahydro-2H-pyran-2-yl)-2-(3-fluoro-6-methoxy-1,5-naphthyridin-4-yl)ethanol Starting from intermediate 3.iii (0.054 g, 0.169 mmol) and 2,3-dihydro-[1,4]dioxino[2,3-c]pyridine-7-carbaldehyde (0.028 g, 1 eq.) and using the procedure of Example 1 (with the only exception that NaBD$_4$ was used as a reducing agent), the title compound was obtained as an off-white foam (0.026 g, 32% yield). The crude product was purified by CC (DCM-MeOH 93:7 containing 0.7% aq. NH$_4$OH).

$^1$H NMR (d6-DMSO) δ: 8.71 (s, 1H); 8.24 (d, J=9.1 Hz, 1H); 7.98 (s, 1H); 7.19 (d, J=9.1 Hz, 1H); 6.90 (s, 1H); 4.52 (d, J=5.9 Hz, 1H); 4.30-4.34 (m, 2H); 4.23-4.27 (m, 2H); 4.00 (s, 3H); 3.85-3.96 (m, 2H); 3.62 (d, J=7.3Hz, 1H); 3.32 (overlapped m, 1H); 3.07-3.16 (m, 2H); 2.90 (t, J=10.3 Hz, 1H); 2.43 (overlapped m, 1H); 2.09-1.94 (m, 2H); 1.65 (m, 1H); 1.48 (m, 1H); 1.18 (m, 1H).

MS (ESI, m/z): 472.4 [M+H$^+$] for $C_{24}H_{26}N_4O_5DF$.

Example 17

(1S)-1-((2S,5R)-5-(((2,3-dihydro-[1,4]dioxino-2,2,3,3-d4-[2,3-c]pyridin-7-yl)methyl)amino)tetrahydro-2H-pyran-2-yl)-2-(3-fluoro-6-methoxy-1,5-naphthyridin-4-yl)ethanol

17.i. (4-(2-bromoethoxy-d4)-5-((4-methoxybenzyl)oxy)pyridin-2-yl)methyl acetate To a solution of 5-((4-methoxybenzyl)oxy)-4-oxo-1,4-dihydropyridin-2-yl)methyl acetate (prepared according to WO 2006/014580; 1.6 g, 5.28 mmol) in DMF (16 mL) was added K$_2$CO$_3$ (1.46 g, 10.5 mmol) and d4-dibromoethane (2.25 mL, 26 mmol). The reaction was stirred at 75° C. for 3 h. The solution was concentrated and the residue was partitioned between water and EA. The aq. layer was extracted several times with EA (5×25 mL). The org. layers were combined, dried over MgSO$_4$ and evaporated to dryness. The oily residue was purified by CC (EA/Hept 1:1 to 4:1 to 1:0), affording the title intermediate as a beige solid (1.49 g, 68% yield).

$^1$H NMR (CDCl$_3$) δ: 8.16 (s, 1H); 7.34-7.38 (m, 2H); 6.88-6.92 (m, 2H); 6.87 (s, 1H); 5.11 (s, 4H); 3.81 (s, 3H); 2.14 (s, 3H).

MS (ESI, m/z): 414.2 [M+H$^+$] for $C_{18}H_{16}NO_5BrD_4$.

17.ii. 4-(2-bromoethoxy-d4)-6-(hydroxymethyl)pyridin-3-ol hydrochloride

A mixture of intermediate 17.i (1.49 g, 3.6 mmol) in an AcOH-conc. HCl mixture (2-1, 15 mL) was heated to 60° C. for 1 h. The solvents were removed in vacuo and the residue was triturated in ether, affording the title compound as a beige solid (1.01 g, 97% yield).

$^1$H NMR (d6-DMSO) δ: 11.36 (br. s, 1H); 8.12 (s, 1H); 7.52 (s, 1H), 4.70 (s, 2H).

17.iii. (2,3-dihydro-[1,4]dioxino-2,2,3,3-d4-[2,3-c]pyridin-7-yl)methanol

To a solution of intermediate 17.ii (1.01 g, 3.50 mmol) in DMF (15 mL) was added K$_2$CO$_3$ (0.968 g, 7.0 mmol). The mixture was heated at 75° C. for 3 h. The solvent was removed in vacuo and the residue was taken up in a minimal amount of water and extracted with EA (5×20 mL). The combined org. layers were dried and evaporated. The residue was purified by CC (DCM-MeOH 97-3), affording the title compound as a white solid (0.5 g, 85% yield).

$^1$H NMR (d6-DMSO) δ: 7.98 (s, 1H); 6.88 (s, 1H); 5.23 (t, J=5.9 Hz, 1H); 4.38 (d, J=5.9 Hz, 1H).

17.iv. 2,3-dihydro-[1,4]dioxino-2,2,3,3-d[2,3-c]pyridine-7-carbaldehyde

To a solution of intermediate 17.iii (508 mg, 2.97 mmol) in DCM (15 mL) was added MnO$_2$ (1.3 g, 14.8 mmol). The reaction mixture was stirred at rt for 24 h, filtered over Celite and washed with DCM (100 mL). The filtrate was concentrated to dryness. The solid was purified by CC (DCM-MeOH 49-1), affording the title aldehyde as a white solid (0.429 g, 85% yield).

$^1$H NMR (d6-DMSO): 9.79 (s, 1H); 8.33 (s, 1H); 7.40 (s, 1H).

17. v. (1S)-1-((2S,5R)-5-(((2,3-dihydro[1,4]dioxino-2,2,3,3-d4-[2,3-c]pyridin-7-yl)methyl)amino)tetrahydro-2H-pyran-2-yl)-2-(3-fluoro-6-methoxy-1,5-naphthyridin-4-yl)ethanol To a solution of intermediate 3.iii (0.207 g, 0.65 mmol) in MeOH (4 mL), was added intermediate 16.iv (0.109 g, 0.65 mmol). The mixture was stirred at rt overnight. NaBH$_4$ (100 mg, 2.58 mmol) was added. The reaction mixture was diluted with DCM (2 mL) and was stirred for 30 min. at rt. Sat. NaHCO$_3$ (5 mL) was added. The volatiles were removed in vacuo. DCM-MeOH 9-1 (10 mL) was added and the two layers were decanted. The aq. layer was extracted twice with DCM-MeOH (9-1, 2×10 mL). The combined org. layers were washed with brine (5 mL), dried over Na$_2$SO$_4$, filtered and concentrated to dryness. The solid residue was purified by CC (EA-MeOH 9-1 then DCM-MeOH 19-1 with 0.5% aq. NH$_4$OH to DCM-MeOH 9-1 with 1% aq. NH$_4$OH) affording the title compound as an off-white foam (0.189 g).

$^1$H NMR (d6-DMSO) δ: 8.72 (s, 1H); 8.24 (d, J=9.1 Hz, 1H); 7.98 (s, 1H); 7.19 (d, J=9.1 Hz, 1H); 6.91 (s, 1H); 4.53 (d, J=6.2 Hz, 1H); 4.00 (s, 3H); 3.85-3.96 (m, 2H); 3.68 (AB system, J=14.4 Hz, Δ=0.05 ppm, 2H); 3.32 (overlapped m, 1H); 3.07-3.16 (m, 2H); 2.90 (t, J=10.3 Hz, 1H); 2.43 (overlapped m, 1H); 2.16 (br. s, 1H); 1.99 (m, 1H); 1.65 (m, 1H); 1.47 (m, 1H); 1.18 (m, 1H).

MS (ESI, m/z): 475.4 [M+H$^+$] for C$_{24}$H$_{23}$N$_4$O$_5$D$_4$F.

Example 18

(1S)-1-((2S,5R)-5-(((2,3-dihydro-[1,4]dioxino[2,3-c]pyridin-7-yl)methyl)amino)tetrahydro-2H-pyran-2-yl)-2-(3-fluoro-6-methoxy-1,5-naphthyridin-4-yl)ethanol-1-d1

18.i. Tert-butyl ((2,3-dihydro-[1,4]dioxino[2,3-c]pyridin-7-yl)methyl)((3R,6S)-6-((1S)-2-(3-fluoro-6-methoxy-1,5-naphthyridin-4-yl)-1-hydroxyethyl)tetrahydro-2H-pyran-3-yl)carbamate To a solution of the compound of Example 3 (500 mg, 0.6 mmol) in DCM (10 mL) was added di-tert-butyl-dicarbonate (418 mg, 1.8 eq.). The mixture was stirred at rt for 3 h. The reaction mixture was directly purified by CC (DCM to DCM-MeOH 9-1 with gradient), affording the title compound as a colourless foam (870 mg, >100% yield, contaminated with remaining reagent).

MS (ESI, m/z): 571.4 [M+H$^+$] for C$_{29}$H$_{35}$N$_4$O$_7$F.

18.ii. Tert-butyl ((2,3-dihydro-[1,4]dioxino[2,3-c]pyridin-7-yl)methyl)((3R,6S)-6-(2-(3-fluoro-6-methoxy-1,5-naphthyridin-4-yl)acetyl)tetrahydro-2H-pyran-3-yl)carbamate To an ice-chilled solution of intermediate 18.i (870 mg, 0.368 mmol) in DCM (4 mL) were added DIPEA (0.55 mL) and a solution of Pyr.SO$_3$ (413 mg, 50% purity, 0.552 mmol) in DMSO (1.4 mL). The mixture was stirred at the same temperature for 20 min. Sat. NaHCO$_3$ (20 mL) was added. The mixture was diluted with DCM (20 mL) and the two layers were decanted. The org. layer was dried over Na$_2$SO$_4$, filtered and concentrated to dryness. The residue was purified by CC (DCM to DCM-MeOH 9-1 with gradient), affording the title compound as a colourless foam (573 mg, 96% yield).

MS (ESI, m/z): 569.4 [M+H$^+$] for C$_{29}$H$_{33}$N$_4$O$_7$F.

18.iii. Tert-butyl ((2,3-dihydro-[1,4]dioxino[2,3-c]pyridin-7-yl)methyl)((3R,6S)-6-((1RS)-2-(3-fluoro-6-methoxy-1,5-naphthyridin-4-yl)-1-hydroxyethyl-1-d1)tetrahydro-2H-pyran-3-yl)carbamate To an ice-chilled solution of intermediate 18.ii (573 g, 1 mmol) in MeOH (9 mL) was added NaBD$_4$ (120 mg, 2.87 mmol) in one portion. The mixture was stirred at the same temperature for 30 min. Sat. NaHCO$_3$ (10 mL) and DCM (30 mL) were added. The two layers were decanted and the org. layer was dried over Na$_2$SO$_4$, filtered and concentrated to dryness. The residue was purified by CC (DCM-MeOH 1-0 to 9-1 with gradient), affording the title compound as a 2-1 mixture of diastereomers in the form of a colourless foam (566 mg, 98% yield).

MS (ESI, m/z): 572.4 [M+H$^+$] for C$_{29}$H$_{34}$N$_4$O$_7$DF.

18.iv. (1S)-1-((2S,5R)-5-(((2,3-dihydro[1,4]dioxino[2,3-c]pyridin-7-yl)methypamino)tetrahydro-2H-pyran-2-yl)-2-(3-fluoro-6-methoxy-1,5-naphthyridin-4-yl)ethanol-1-d1

Starting from intermediate 18.iii (566 mg, 0.98 mmol), the title compound (412 mg, 88% yield) was obtained as a 2-1 mixture of diastereomers using the procedure of Example 3, step 3.iii. The mixture of diastereomers (212 mg), was separated by semi preparative chiral HPLC on a Daicel ChiralPak AI column (20×250 mm), eluting with MeCN:EtOH:diisopropylamine 30:70:0.1 (flow rate 16 mL/min, UV detection at 210 nM), affording respectively 64 mg and 114 mg of each diastereomer. Analytical samples were eluted on a ChiralPack AI (4.6×250 mm, 5 μM) column at a flow rate of 0.8 mL/min using the aforementioned eluent. The respective retention times were 8.8 and 10.98 min. The title enantiomer (white solid) was identified as the major second eluting compound.

$^1$H NMR (d6-DMSO) δ: 8.72 (s, 1H); 8.25 (d, J=9.1 Hz, 1H); 7.98 (s, 1H); 7.19 (d, J=9.1 Hz, 1H); 6.91 (s, 1H); 4.51 (s, 1H); 4.30-4.34 (m, 2H); 4.24-4.28 (m, 2H); 4.00 (s, 3H); 3.93 (m, 1H); 3.60-3.70 (m, 2H); 3.32 (overlapped m, 1H); 3.07-3.15 (m, 2H); 2.90 (t, J=10.3 Hz, 1H); 2.43 (overlapped m, 1H); 1.95-2.05 (m, 2H); 1.64 (m, 1H); 1.48 (m, 1H); 1.19 (m, 1H).

MS (ESI, m/z): 472.5 [M+H$^+$] for C$_{24}$H$_{26}$N$_4$O$_5$DF

Example 19

(S)-1-((2S,5R)-5-(((2,3-dihydro-[1,4]oxathiino[2,3-c]pyridin-7-yl)methyl-d1)amino)tetrahydro-2H-pyran-2-yl)-2-(3-fluoro-6-methoxy-1,5-naphthyridin-4-yl)ethanol To a solution of intermediate 3.iii (80 mg, 0.25 mmol) in MeOH (1.5 mL), was added 2,3-dihydro-[1,4]oxathiino[2,3-c]pyridine-7-carbaldehyde (45 mg, 1.01 eq.). The mixture was stirred at rt overnight. After cooling to 0° C., NaBD$_4$ (62 mg, 1.5 mmol) and DCM (0.5 mL) were added. The reaction mixture was stirred 2.5 h, the reaction mixture being allowed to reach rt. DCM (8 mL) and sat. NaHCO$_3$ (8 mL) were added. The two layers were decanted and the aq. layer was extracted with DCM-MeOH (9-1, 2×10 mL). The combined org. layers were dried over Na$_2$SO$_4$, filtered and concentrated to dryness. The residue was purified by CC (EA-MeOH 9-1 then DCM-MeOH 19-1 with 0.5% aq. NH$_4$OH to DCM-MeOH 93-7 with 0.7% aq. NH$_4$OH), affording the title compound as a white foam (0.1 g, 80% yield).

$^1$H NMR (d6-DMSO) δ: 8.72 (s, 1H); 8.25 (d, J=9.1 Hz, 1H); 7.92 (s, 1H); 7.19 (d, J=9.1 Hz, 1H); 7.13 (s, 1H); 4.53

(d, J=5.9 Hz, 1H); 4.33-4.38 (m, 2H); 4.01 (s, 3H); 3.87-3.96 (m, 2H); 3.63 (d, J=9.4 Hz, 1H); 3.31 (overlapped m, 1H); 3.22-3.26 (m, 2H); 3.07-3.16 (m, 2H); 2.90 (t, J=10.3 Hz, 1H); 2.43 (overlapped m, 1H); 2.19 (br. s, 1H); 2.01 (m, 1H); 1.67 (m, 1H); 1.49 (m, 1H); 1.19 (m, 1H).

MS (ESI, m/z): 472.4 [M+H$^+$] for $C_{24}H_{26}N_4O_4DFS$.

Example 20

(1S)-1-((2S,5R)-5-(((2,3-dihydro-[1,4]dioxino-[2,3-c]pyridin-7-yl)methyl)amino)tetrahydro-2H-pyran-2-yl)-2-(3-fluoro-6-methoxy-1,5-naphthyridin-4-yl)ethanol-2-d1

20.i. Tert-butyl ((3R,6S)-6-((S)-2-(3-fluoro-6-methoxy-1,5-naphthyridin-4-yl)-1-hydroxyethyl-2-d1) tetrahydro-2H-pyran-3-yl)carbamate NaBD$_4$ (130 mg, 3.1 mmol) was suspended in ethanol-d6 (7 mL). Pd$_2$(dba)$_3$ (0.013 g, 0.015 mmol) was added as a solid. The mixture was cooled to 10° C. and a solution of intermediate 3.i (850 mg, 1.83 mmol) in THF (2.5 mL) was then added dropwise, keeping the internal temperature below 20° C. After 30 min, the reaction mixture was allowed to warm up to rt. At this point, the mixture was cooled down to 0° C. and water (10 mL) was added. The solution was filtered on Celite and washed with EA (20 mL). The aq. layer was extracted with EA (30 mL). The org. layers were combined, dried over Na$_2$SO$_4$, filtered and concentrated to dryness. The residue was purified by CC (Hept-EA 2-1 to Hept-EA 1-2), affording the title compound as a yellow oil (360 mg, 46% yield).

MS (ESI, m/z): 423.4 [M+H$^+$] for $C_{24}H_{26}N_4O_4DFS$.

20.ii. (S)-1-((2S,5R)-5-aminotetrahydro-2H-pyran-2-yl)-2-(3-fluoro-6-methoxy-1,5-naphthyridin-4-yl)ethanol-2-d1

Starting form intermediate 20.i (360 mg, 0.854 mmol) and using the procedure of Example 3, step 3.iii, the title compound was obtained as a yellow solid (84 mg, 31% yield). The compound was purified by CC (DCM-MeOH 9-1 with 1% aq. NH$_4$OH).

MS (ESI, m/z): 323.6 [M+H$^+$] for $C_{16}H_{19}N_3O_3DF$.

20.iii. (1S)-1(2S,5R)-5-(((2,3-dihydro-[1,4]dioxino-[2,3-c]pyridin-7-yl)methyl)amino)tetrahydro-2H-pyran-2-yl)-2-(3-fluoro-6-methoxy-1,5-naphthyridin-4-yl)ethanol-2-d1

Starting from intermediate 20.ii (80 mg, 0.249 mmol) and 2,3-dihydro-[1,4]dioxino[2,3-c]pyridine-7-carbaldehyde (41 mg, 1 eq.) and using the procedure of Example 1, the title compound was obtained as an white solid (29 mg, 25% yield). The crude product was purified by CC (eluent: DCM-MeOH 93-7 with 0.7% aq. NH$_4$OH).

$^1$H NMR (d6-DMSO) δ: 8.72 (s, 1H); 8.25 (d, J=9.1 Hz, 1H); 7.99 (s, 1H); 7.19 (d, J=9.1 Hz, 1H); 6.91 (s, 1H); 4.53 (dd, J=2.3, 6.2 Hz, 1H); 4.30-4.34 (m, 2H); 4.24-4.28 (m, 2H); 4.00 (s, 3H); 3.85-3.96 (m, 2H); 3.63-3.67 (m, 2H); 3.07-3.16 (m, 2H); 2.90 (t, J=10.8 Hz, 1H); 2.44 (overlapped m, 1H); 1.95-2.11 (m, 2H); 1.65 (m, 1H); 1.48 (m, 1H); 1.18 (m, 1H).

MS (ESI, m/z): 472.4 [M+H$^+$] for $C_{24}H_{26}N_4O_5DF$.

Example 21

(S)-1-((2S,5R)-5-(((2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-2-d1

Starting from intermediate 20.ii (20 mg, 0.062 mmol) and 2,3-dihydro-[1,4]oxathiino[2,3-c]pyridine-7-carbaldehyde (11 mg, 1 eq.) and using the procedure of Example 1, the title compound was obtained, after purification by CC (eluent: DCM-MeOH 93-7 containing 0.7% aq. NH$_4$OH), as a white solid (17 mg, 55% yield).

MS (ESI, m/z): 488.8 [M+H$^+$] for $C_{24}H_{26}N_4O_4DFS$.

Example 22

(S)-((1S,5R)-5-(((2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-1-d1

Starting from the compound of Example 6 (475 mg, 0.976 mmol) and using the procedures of Example 18, steps 18.i to 18.iv (Boc formation: 100% yield; alcohol oxidation: 96% yield; ketone reduction with NaBD$_4$: 96% yield; Boc deprotection: 85% yield), the title compound was obtained as a colourless foam (198 mg). If necessary, the crude substances of the 3 first steps were purified by CC using an appropriate eluent. The product of the fourth step was obtained as a 1.5-1 mixture of diastereomers. Said mixture of diastereomers was separated by semi preparative chiral HPLC on a Daicel ChiralPak AI column (20×250 mm) eluting with MeCN:EOH:diisopropylamine 10:90:0.1 (flow rate 16 mL/min, UV detection at 210 nM), affording respectively 62 mg and 97 mg of each diastereomer. Analytical samples were eluted on a ChiralPack AI (4.6×250 mm, 5 μM) column at a flow rate of 0.8 mL/min using the aforementioned eluent. The respective retention times were 14.8 and 19.2 min. The title enantiomer (white foam) was identified as the major second eluting compound.

$^1$H NMR (d6-DMSO) δ: 8.72 (s, 1H); 8.25 (d, J=9.1 Hz, 1H); 7.92 (s, 1H); 7.19 (d, J=9.1 Hz, 1H); 7.13 (s, 1H); 4.51 (s, 1H); 4.33-4.38 (m, 2H); 4.00 (s, 3H); 3.93 (m, 1H); 3.60-3.70 (m, 2H); 3.31 (overlapped m, 1H); 3.22-3.26 (m, 2H); 3.06-3.16 (m, 2H); 2.90 (t, J=10.5 Hz, 1H); 2.43 (overlapped m, 1H); 1.96-2.08 (m, 2H); 1.63 (m, 1H); 1.48 (m, 1H); 1.19 (m, 1H).

MS (ESI, m/z): 488.7 [M+H$^+$] for $C_{24}H_{26}N_4O_4DFS$.

Example 23

(S)-1-{(2S,5R)-5-[(6,7-dihydro-8-oxa-5-thia-1,2-diaza-naphthalen-3-ylmethyl-d1)-amino]-tetrahydro-pyran-2-yl}-2-(3-fluoro-6-methoxy-[1,5]naphthyridin-4-yl)-ethanol Starting from intermediate 3.iii (84 mg, 0.249 mmol) and 6,7-dihydro-[1,4]oxathiino[2,3-c]pyridazine-3-carbaldehyde (45 mg, 1 eq.) and using the procedure of Example 1 (with the only exception that NaBD$_4$ was used as the reducing agent), the title compound was obtained as an off-white foam (76 mg, 62% yield). The crude product was purified by CC (DCM-MeOH 93:7 containing 0.7% aq. NH$_4$OH).

¹H NMR (d6-DMSO) δ: 8.72 (s, 1H); 8.25 (d, J=9.1 Hz, 1H); 7.53 (s, 1H); 7.19 (d, J=9.1 Hz, 1H); 4.51-4.62 (m, 3H); 4.00 (s, 3H); 3.86-3.97 (m, 2H); 3.79 (d, J=7.9 Hz, 1H); 3.26-3.33 (m, 3H); 3.07-3.16 (m, 2H); 2.90 (t, J=10.5 Hz, 1H); 2.43 (overlapped m, 1H); 1.95-2.06 (m, 2H); 1.65 (m, 1H); 1.49 (m, 1H); 1.18 (m, 1H).
MS (ESI, m/z): [M+H⁺] for $C_{23}H_{25}N_5O_4DFS$.

Example 24

(1S)-1-((2S,5R)-5-(((2,3-dihydro-[1,4]dioxino [2,3-c]pyridin-7-yl)methyl-d2)amino)tetrahydro-2H-pyran-2-yl)-2-(3-fluoro-6-methoxy-1,5-naphthyridin-4-yl)ethanol 24.i. 2,3-dihydro[1,4]dioxino[2,3-c]pyridine-7-carboxylic acid To a solution of 2,3-dihydro-[1,4]dioxino[2,3-c]pyridine-7-carbaldehyde (722 mg, 4.37 mmol) in 2-methyl-2-propanol (95 mL) and 2-methyl-2-butene (22 mL) was added dropwise a solution of sodium chlorite (80%, 4.55 g, 40.22 mmol) and sodium dihydrogenphosphate (3.65 g, 26.45 mmol) in water (35 mL). The resulting solution was stirred at rt for 19 h. The volatiles were removed under reduced pressure. The residue was diluted with water (20 mL) and pH was adjusted to 3 by addition of 1N HCl. The aq. layer was extracted with DCM-MeOH 9-1 (25×30 mL). The combined extracts were dried over $Na_2SO_4$, filtered and evaporated under reduced pressure. The residue was triturated in ether and filtered to give the title acid as a white solid (0.405 g, 51% yield).
¹H NMR (d6-DMSO) δ: 8.19 (s, 1H); 7.50 (s, 1H); 4.36 (s, 4H).
MS (ESI, m/z): 182.3 [M+H⁺] for $C_8H_7NO_4$.

24.ii. N-methoxy-N-methyl-2,3-dihydro-[1,4]dioxino[2,3-c]pyridine-7-carboxamide

To an ice-chilled suspension of intermediate 24.i (402 mg, 2.22 mmol) in DCM (5.5 mL) were added N,O-dimethylhydroxylamine hydrochloride (98%, 246 mg, 2.47 mmol), DIPEA (1.52 mL, 8.87 mmol) and T3P (50% in EA, 1.46 mL, 2.48 mmol) dropwise. The reaction was stirred at 0° C. for 30 min before warming to rt. The reaction proceeded overnight. The reaction mixture was washed twice with sat. sodium bicarbonate (2×10 mL). The aqueous layer (basified with 1 mL of sat. aq. $Na_2CO_3$) was then extracted with DCM-MeOH 9-1 (3×10 mL). The combined org. layers were dried over $Na_2SO_4$, filtered and evaporated under reduced pressure. The residue was purified by CC (DCM-MeOH with gradient) to give the title compound as an off-white solid (396 mg, 80% yield).
¹H NMR (d6-DMSO) δ: 8.10 (s, 1H); 7.10 (s, 1H); 4.31-4.41 (m, 4H); 3.65 (s, 3H);
3.24 (s, 3H).
MS (ESI, m/z): 225.1 [M+H⁺] for $C_{10}H_{12}N_2O_4$.

24.iii. 2,3-dihydro-[1,4]dioxino[2,3-c]pyridine-7-carbaldehyde-d1

To a solution of intermediate 24.ii (202 mg, 0.90 mmol) in THF (5.5 mL) cooled at −78° C. was added $LiAlD_4$ (98% D, 49 mg, 1.14 mmol). The resulting mixture was stirred at the same temperature for 1 h. The reaction mixture was diluted with THF (15 mL) and a sat. $Na_2SO_4$ solution (1 mL) was added. The suspension was filtered and the filtrate was evaporated under reduced pressure. The residue was purified by CC (DCM-MeOH with gradient) to give the title aldehyde as a white solid (131 mg, 87% yield).
¹H NMR (d6-DMSO) δ: 8.32 (s, 1H); 7.40 (s, 1H); 4.40 (m, 4H).
MS (ESI, m/z): 167.1 [M+H⁺] for $C_8H_6NO_3D$.

24.iv. (1S)-1-((2S,5R)-5-(((2,3-dihydro-[1,4]dioxino [2,3-c]pyridin-7-yl)methyl-d2)amino)tetrahydro-2H-pyran-2-yl)-2-(3-fluoro-6-methoxy-1,5-naphthyridin-4-yl)ethanol Starting from intermediate 3.iii (104 mg, 0.32 mmol) and intermediate 24.iii (45 mg, 1.02 eq.) and using the procedure of Example 1 (with the only exception that $NaBD_4$ was used as the reducing agent), the title compound was obtained, after purification by CC (DCM-MeOH 93:7 containing 0.7% aq. $NH_4OH$), as an off-white foam (79 mg, 52% yield).
¹H-NMR (d6-DMSO) δ: 8.72 (s, 1H); 8.24 (d, J=9.1 Hz, 1H); 7.98 (s, 1H); 7.19 (d, J=9.1 Hz, 1H); 6.91 (s, 1H); 4.53 (d, J=5.9 Hz, 1H); 4.31-4.34 (m, 2H); 4.23-4.27 (m, 2H); 4.00 (s, 3H); 3.85-3.96 (m, 2H); 3.32 (overlapped m, 1H); 3.07-3.16 (m, H); 2.90 (t, J=10.3 Hz, 1H); 2.43 (overlapped m, 1H); 2.09-1.94 (m, 2H); 1.65 (m, 1H); 1.48 (m, 1H); 1.18 (m, 1H).
MS (ESI, m/z): 473.6 [M+H⁺] for $C_{24}H_{25}N_4O_5D_2F$.

Pharmacological Properties of the Invention Compounds
In vitro assays
1) Bacterial Growth Minimal Inhibitory Concentrations:
Experimental Methods:
Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7th ed., Clinical and Laboratory Standards Institute (CLSI) Document M7-A7, Wayne, Pa., USA, 2006.
Results:
All Example compounds were tested against several Gram positive and Gram negative bacteria.
Typical antibacterial test results are given in the table hereafter (MIC in mg/l).

| Example No. | MIC for S. aureus A798 | Example No. | MIC for S. aureus A798 |
|---|---|---|---|
| 1 | ≦0.031 | 2 | 0.25 |
| 3 | ≦0.031 | 4 | ≦0.031 |
| 5 | ≦0.031 | 6 | ≦0.031 |
| 7 | ≦0.031 | 8 | ≦0.031 |
| 9 | ≦0.031 | 10 | ≦0.031 |
| 11 | ≦0.031 | 12 | ≦0.031 |
| 13 | ≦0.031 | 14 | ≦0.031 |
| 15 | ≦0.031 | 16 | ≦0.031 |
| 17 | ≦0.031 | 18 | ≦0.031 |
| 19 | ≦0.031 | 20 | ≦0.031 |
| 21 | ≦0.031 | 22 | ≦0.031 |
| 23 | ≦0.031 | 24 | ≦0.031 |

2) In Vitro Blocking of hERG K⁺ Channels:
Principle:
Drug-induced prolongation of the QT interval and resultant ventricular dysrhythmia, including torsades de pointes, is an adverse event which occurs among other drugs, within some members of various classes of anti-infective agents. During recent years, there have been numerous antibacterials either withdrawn from the market or abandoned in various phases of clinical development due to their potential to cause this life-threatening toxicity. Anti-infective agents warrant particular attention, as these are used in rather high concentrations and frequently added to complicated drug regimens when complete information regarding a drug regimen may be lacking Certain anti-infective drug classes, such as the macrolides and quinolones as well as the recently disclosed Viquidacin which belongs to the same chemical classes as the compounds of the present invention, have all been implicated. In fact, the ability to prolong the QT interval often varies among members of these drug classes and the potential for this effect cannot be predicted accurately during drug design and development. The best predictor is the extent of the hERG K$^+$ channel blockade. Although some predictive models for hERG inhibition have been developed, there is today no clear Structure-Activity Relationship to predict such an inhibition. We have discovered that combining two features of the present invention leads to compounds with reduced hERG liabilities while maintaining the level of antibacterial activity.

Experimental Methods:

hERG K$^+$ channels have been cloned from human heart and recombinant channels are stably expressed in CHO-K1 cells (CHO$_{hERG}$). These cells have been purchased from bSys GmbH (CH-4052 Basel, Switzerland) and are grown in 150 mL culture flasks at 37° C. in 5% CO$_2$. When the cells are ~100% confluent, they are detached with 0.25% trypsin-EDTA solution and placed in the cell preparation unit of a QPatch automated patch-clamp robot (Sophion Bioscience A/S, 2750 Ballerup, Denmark). Currents through the hERG K$^+$ channels (IK$_{hERG}$) are elicited using the following buffer solutions and voltage protocol:

extracellular solution (in mM): [NaCl]=150; [KCl]=4; [CaCl$_2$]=1.2; [MgCl$_2$]=1; [HEPES]=10; pH adjusted to 7.4 with NaOH;

intracellular solution (in mM): [KCl]=140; [NaCl]=10; [MgCl$_2$]=1; [HEPES]=10; [EGTA]=5; [Mg-ATP]=5; [Na$_3$-GTP]=0.1; pH adjusted to 7.2 with KOH;

voltage protocol: the resting potential is −80 mV and the frequency of stimulation is 0.1 Hz. hERG K$^+$ currents are measured as the average current during the last 20 ms of the 500 ms pulse to −40 mV minus the average current during the last 20 ms of the 50 ms pulse to −40 mV.

After the cells have stabilized for a few minutes and the currents are steady, the amplitude of IK$_{hERG}$ is recorded under control conditions. Thereafter, the QPatch robot applies the test compound to the cell at the test concentration and, after 4 minutes of stimulation, the amplitude of IK$_{hERG}$ is recorded under test conditions. The ratio of the two amplitudes is used to define a fractional block and the average block on two cells is used to provide the effect of a given concentration (e.g. 10 μM). If, for a given test compound, a sufficient number of concentrations were tested, an apparent IC$_{50}$ for inhibition of IK$_{hERG}$ is calculated.

Results:

Testing the compounds having the formula I$_{COMP}$ shown below

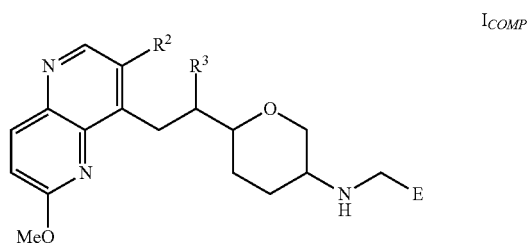

I$_{COMP}$ using the experimentals methods described above for the MIC regarding *S. aureus* A798 bacteria and for in vitro blocking hERG K$^+$ channels gave the results summarised in the table hereafter.

| Example No. or Reference Example No. | R$^2$ | R$^3$ | E | MIC for *S. aureus* A798 | % inhibition hERG (at 10 μM) |
|---|---|---|---|---|---|
| Example No. 1 | H | OH | | ≦0.031 | 26 |
| Example No. 3 | F | OH | | ≦0.031 | 29 |
| Reference Example No. 1 [=compound of formula (E1)] | F | H | | ≦0.031 | 77 |
| Example No. 4 | F | OH | | ≦0.031 | 5 |

| Example No. or Reference Example No. | R² | R³ | E | MIC for S. aureus A798 | % inhibition hERG (at 10 µM) |
|---|---|---|---|---|---|
| Reference Example No. 2 | F | OH | 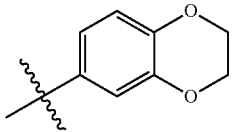 | ≦0.031 | 85 |

The invention claimed is:

1. A compound of formula I

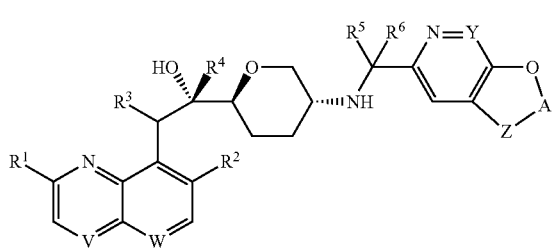

wherein
R¹ represents alkoxy;
R² represents H or F;
each of R³, R⁴, R⁵, and R⁶ represents independently H or D;
V represents CH and W represents CH or N, or V represents N and W represents CH;
Y represents CH or N;
Z represents O, S, or CH₂; and
A represents CH₂, CH₂CH₂, or CD₂CD₂;
or a salt thereof.

2. The compound according to claim 1, wherein each of R³, R⁴, R⁵, and R⁶ represents H, and A represents CH₂ or CH₂CH₂; or a salt thereof.

3. The compound according to claim 1, wherein:
R¹ represents (C₁-C₃)alkoxy; and
at most one of R³, R⁴, R⁵, and R⁶ represents D and A represents CH₂ or CH₂CH₂, or each of R³, R⁴, R⁵, and R⁶ represents H and A represents CH₂, CH₂CH₂, or CD₂CD₂;
or a salt thereof.

4. The compound according to claim 1, which is a compound of formula I_P

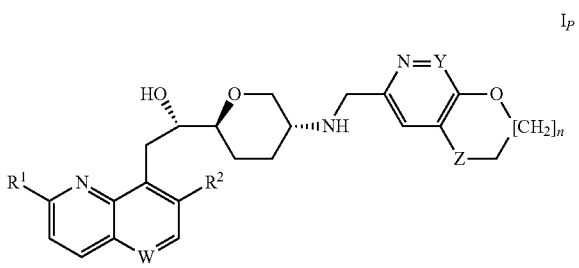

wherein
R¹ represents alkoxy;
R² represents H or F;
W represents CH or N;
Y represents CH or N;
Z represents O, S, or CH₂; and
n represents 0 or 1;
or a salt thereof.

5. The compound according to claim 1, wherein R¹ is methoxy; or a salt thereof.

6. The compound according to claim 1, wherein R² represents H; or a salt thereof.

7. The compound according to claim 1, wherein R² represents F; or a salt thereof.

8. The compound according to claim 1, wherein W represents N; or a salt thereof.

9. The compound according to claim 1, wherein W represents CH; or a salt thereof.

10. The compound according to claim 1, wherein Y represents CH; or a salt thereof.

11. The compound according to claim 1, wherein Y represents N; or a salt thereof.

12. The compound according to claim 1, which is:
(1S)-1-{(2S,5R)-5-[(2,3-dihydro-[1,4]dioxino[2,3-c]pyridin-7-ylmethyl)-amino]-tetrahydro-pyran-2-yl}-2-(6-methoxy-[1,5]naphthyridin-4-yl)-ethanol;
(1S)-1-{(2S,5R)-5-[(6,7-dihydro-[1,4]dioxino[2,3-c]pyridazin-3-ylmethyl)-amino]-tetrahydro-pyran-2-yl}-2-(6-methoxy-[1,5]naphthyridin-4-yl)-ethanol;
(1S)-1-{(2S,5R)-5-[(2,3-dihydro-[1,4]dioxino[2,3-c]pyridin-7-ylmethyl)-amino]-tetrahydro-pyran-2-yl}-2-(3-fluoro-6-methoxy-[1,5]naphthyridin-4-yl)-ethanol;
(1S)-1-{(2S,5R)-5-[(6,7-dihydro-[1,4]dioxino[2,3-c]pyridazin-3-ylmethyl)-amino]-tetrahydro-pyran-2-yl}-2-(3-fluoro-6-methoxy-[1,5]naphthyridin-4-yl)-ethanol;
(1S)-1-{(2S,5R)-5-[(2,3-dihydro-[1,4]dioxino[2,3-c]pyridin-7-ylmethyl)-amino]-tetrahydro-pyran-2-yl}-2-(7-fluoro-2-methoxy-quinolin-8-yl)ethanol;
(1S)-1-{(2S,5R)-5-[(2,3-dihydro-4-oxa1-thia-6-aza-naphthalen-7-ylmethyl)-amino]-tetrahydro-pyran-2-yl}-2-(3-fluoro-6-methoxy-[1,5]naphthyridin-4-yl)-ethanol;
(1S)-1-{(2S,5R)-5-[(2,3-dihydro-4-oxa-1-thia-6-aza-naphthalen-7-ylmethyl)-amino]-tetrahydro-pyran-2-yl}-2-(7-fluoro-2-methoxy-quinolin-8-yl)-ethanol;
(1S)-2-(3-fluoro-6-methoxy-[1,5]naphthyridin-4-yl)-1-{(2S,5R)-5-[(3-oxa-1-thia-5-aza-indan-6-ylmethyl)-amino]-tetrahydro-pyran-2-yl}-ethanol;
(1S)-2-(7-fluoro-2-methoxy-quinolin-8-yl)-1-{(2S,5R)-5-[(3-oxa-1-thia-5-aza-indan-6-ylmethyl)-amino]-tetrahydro-pyran-2-yl}-ethanol;
(1S)-1-{(2S,5R)-5-[(3,4-dihydro-2H-pyrano[2,3-c]pyridin-6-ylmethyl)-amino]-tetrahydro-pyran-2-yl}-2-(3-fluoro-6-methoxy-[1,5]naphthyridin-4-yl)-ethanol;
(1S)-1-{(2S,5R)-5-[(6,7-dihydro-8-oxa-5-thia-1,2-diaza-naphthalen-3-ylmethyl)-amino]-tetrahydro-pyran-2-yl}-2-(3-fluoro-6-methoxy-[1,5]naphthyridin-4-yl)-ethanol;

(1S)-1-{(2S,5R)-5-[(2,3-dihydro-[1,4]dioxino[2,3-c]pyridin-7-ylmethyl)-amino]-tetrahydro-pyran-2-yl}-2-(6-fluoro-3-methoxy-quinoxalin-5-yl)-ethanol;

(1S)-1-{(2S,5R)-5-[(6,7-dihydro-[1,4]dioxino[2,3-c]pyridazin-3-ylmethyl)-amino]-tetrahydro-pyran-2-yl}-2-(6-fluoro-3-methoxy-quinoxalin-5-yl-ethanol;

(1S)-1-{(2S,5R)-5-[(2,3-dihydro-4-oxa-1-thia-6-aza-naphthalen-7-ylmethyl)-amino]-tetrahydro-pyran-2-yl}-2-(6-fluoro-3-methoxy-quinoxalin-5-yl)-ethanol;

(1S)-1-{(2S,5R)-5-[(6,7-dihydro-8-oxa-5-thia-1,2-diaza-naphthalen-3-ylmethyl)-amino]-tetrahydro-pyran-2-yl}-2-(6-fluoro-3-methoxy-quinoxalin-5-yl)-ethanol;

(1S)-1-((2S,5R)-5-(((2,3-dihydro-[1,4]dioxino[2,3-c]pyridin-7-yl)methyl-d1)amino)tetrahydro-2H-pyran-2-yl)-2-(3-fluoro-6-methoxy-1,5-naphthyridin-4-yl)ethanol;

(1S)-1-((2S,5R)-5-(((2,3-dihydro[1,4]dioxino-2,2,3,3-d4-[2,3-c]pyridin-7-yl)methyl)amino)tetrahydro-2H-pyran-2-yl)-2-(3-fluoro-6-methoxy-1,5-naphthyridin-4-yl)ethanol;

(1S)-1-(2S,5R)-5(((2,3-dihydro-[1,4]dioxino[2,3-c] pyridin-7-yl)methyl)amino)tetrahydro-2H-pyran-2-yl)-2-(3-fluoro-6-methoxy-1,5-naphthyridin-4-yl)ethanol-1-d1;

(S)-1-((2S,5R)-5-(((2,3-dihydro-[1,4]oxathiino[2,3-c]pyridin-7-yl)methyl-d1)amino)tetrahydro-2H-pyran-2-yl)-2-(3-fluoro-6-methoxy-1,5-naphthyridin-4-yl)ethanol;

(1S)-1-((2S,5R)-5-(((2,3-dihydro-[1,4]dioxino-[2,3-c]pyridin-7-yl)methyl)amino)tetrahydro-2H-pyran-2-yl)-2-(3-fluoro-6-methoxy-1,5-naphthyridin-4-yl)ethanol-2-d1;

(S)-1-((2S,5R)-5-(((2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-2-d1;

(S)-1-((2S,5R)-5-4(2,3-dihydro-[1,4]oxathiino[2,3-c]pyridin-7-yl)methyl)amino)tetrahydro-2H-pyran-2-yl)-2-(3-fluoro-6-methoxy-1,5-naphthyridin-4-yl)ethanol-1-d1;

(S)-1-{(2S,5R)-5-[(6,7-dihydro-8-oxa-5-thia-1,2-diaza-naphthalen-3-ylmethyl-d1)-amino]-tetrahydro-pyran-2-yl}-2-(3-fluoro-6-methoxy-[1,5]naphthyridin-4-yl)-ethanol; or (1S)-1-((2S,5R)-5-(((2,3-dihydro-[1,4]dioxino [2,3-c]pyridin-7-yl)methyl-d2)amino)tetrahydro-2H-pyran-2-yl)-2-(3-fluoro-6-methoxy-1,5-naphthyridin-4-yl)ethanol;

or a salt thereof.

13. A pharmaceutical composition comprising, as an active principle, the compound according to claim 1, or a pharmaceutically acceptable salt thereof, and at least one therapeutically inert excipient.

14. A method for treating a bacterial infection caused by *Staphylococcus aureus* comprising administering to a subject in need thereof, the compound according to claim 1, or a pharmaceutically acceptable salt thereof.

15. A compound according to claim 1, which is (1S)-1-{(2S,5R)-5-[(6,7-dihydro-8-oxa-5-thia-1,2-diaza-naphthalen-3-ylmethyl)-amino]-tetrahydro-pyran-2-yl}-2-(3-fluoro-6-methoxy-[1,5]naphthyridin-4-yl)-ethanol; or a salt thereof.

16. A pharmaceutical composition comprising, as an active principle, the compound according to claim 15, or a pharmaceutically acceptable salt thereof, and at least one therapeutically inert excipient.

17. A method for treating a bacterial infection caused by *Staphylococcus aureus* comprising administering to a subject in need thereof, the compound according to claim 15, or a pharmaceutically acceptable salt thereof.

* * * * *